(12) United States Patent
Kunimoto

(10) Patent No.: US 10,669,660 B2
(45) Date of Patent: Jun. 2, 2020

(54) METHOD FOR PRODUCING A MIXED FIBER SPUNBONDED NONWOVEN WEB

(71) Applicant: MITSUI CHEMICALS, INC., Minato-ku, Tokyo (JP)

(72) Inventor: Naosuke Kunimoto, Yokkaichi (JP)

(73) Assignee: MITSUI CHEMICALS, INC., Minato-Ku, Tokyo (JP)

( * ) Notice: Subject to any disclaimer, the term of this patent is extended or adjusted under 35 U.S.C. 154(b) by 354 days.

(21) Appl. No.: 15/845,579

(22) Filed: Dec. 18, 2017

(65) Prior Publication Data

US 2018/0105966 A1 Apr. 19, 2018

Related U.S. Application Data

(62) Division of application No. 13/384,721, filed as application No. PCT/JP2010/062331 on Jul. 22, 2010, now abandoned.

(30) Foreign Application Priority Data

Aug. 5, 2009 (JP) ................................. 2009-182673
Feb. 4, 2010 (JP) ................................. 2010-023197

(51) Int. Cl.
*D01F 1/10* (2006.01)
*D01F 6/06* (2006.01)
(Continued)

(52) U.S. Cl.
CPC ........... *D04H 3/153* (2013.01); *A61F 13/513* (2013.01); *A61F 13/51104* (2013.01); (Continued)

(58) Field of Classification Search
CPC .. D01D 5/082; D01F 1/10; D01F 6/06; D01F 6/70; D02G 3/045; D04H 3/007; D04H 3/009; D04H 3/153; D04H 3/16
(Continued)

(56) References Cited

U.S. PATENT DOCUMENTS 4,107,364 A 9/1978 Sisson
4,209,563 A 6/1980 Sission
(Continued)

FOREIGN PATENT DOCUMENTS

CH 455699 7/1968
CN 1342221 A 3/2002
(Continued)

OTHER PUBLICATIONS

Chinese Office Action dated Aug. 6, 2014, issued by the State Intellectual Property Office of People's Republic of China in corresponding Chinese Application No. 201080034285.0. (8 pgs.).
(Continued)

*Primary Examiner* — Leo B Tentoni
(74) *Attorney, Agent, or Firm* — Buchanan Ingersoll & Rooney PC

(57) ABSTRACT

A mixed fiber spunbonded nonwoven fabric which comprises 90 to 10% by weight of a long fiber of thermoplastic resin (A) that has been hydrophilization-treated and 10 to 90% by weight of a long fiber of thermoplastic elastomer (B) and which has a strength ratio [the ratio of a strength at 20% of an elongation at a maximum strength (elongation at a maximum point) to the maximum strength] in at least one direction of not more than 40% and a bulk density of 0.10 to 0.40 g/cm$^3$. The fabric can exhibit excellent initial hydrophilicity, long-lasting hydrophilicity, liquid dispersibility, liquid transpiration property, moisture permeability, breathability, softness, resistance to fluff, stretchability and touch, and low stickiness, and is suitable for sheets constituting absorbent articles such as sanitary napkins, panty liners, incontinence pads, and disposable diapers. A production method is also provided.

6 Claims, 4 Drawing Sheets

(51) Int. Cl.

| | | |
|---|---|---|
| *D01F 6/70* | (2006.01) | |
| *D04H 3/153* | (2012.01) | |
| *A61F 13/511* | (2006.01) | |
| *A61F 13/513* | (2006.01) | |
| *A61F 13/514* | (2006.01) | |
| *D01D 5/08* | (2006.01) | |
| *D01D 5/098* | (2006.01) | |
| *D04H 3/16* | (2006.01) | |
| *D04H 3/007* | (2012.01) | |
| *D04H 3/009* | (2012.01) | |
| *D02G 3/04* | (2006.01) | |

(52) U.S. Cl.
CPC .. *A61F 13/51121* (2013.01); *A61F 13/51401* (2013.01); *A61F 13/51466* (2013.01); *A61F 13/51476* (2013.01); *D01D 5/082* (2013.01); *D01D 5/0985* (2013.01); *D02G 3/045* (2013.01); *D04H 3/007* (2013.01); *D04H 3/009* (2013.01); *D04H 3/16* (2013.01); *Y10T 442/681* (2015.04)

(58) Field of Classification Search
USPC .......... 264/103, 210.2, 210.3, 210.6, 211.13, 264/211.18, 211.2, 288.4, 289.3, 342 RE
See application file for complete search history.

(56) References Cited

U.S. PATENT DOCUMENTS

| | | | |
|---|---|---|---|
| 4,798,603 | A | 1/1989 | Meyer et al. |
| 6,863,762 | B2 | 3/2005 | Sanada et al. |
| 8,137,790 | B2 | 3/2012 | Dharmadhikary et al. |
| 2002/0133131 | A1 | 9/2002 | Rangachari |
| 2005/0159067 | A1 | 7/2005 | Kunimoto et al. |
| 2006/0121812 | A1 | 6/2006 | Suzuki et al. |
| 2006/0292954 | A1 | 12/2006 | Suzuka et al. |
| 2009/0035527 | A1 | 2/2009 | Kobayashi et al. |
| 2010/0137824 | A1 | 6/2010 | Uematsu et al. |
| 2011/0092936 | A1 | 4/2011 | Kunimoto |

FOREIGN PATENT DOCUMENTS

| | | |
|---|---|---|
| CN | 1353043 | 6/2002 |
| CN | 1511018 A | 7/2004 |
| CN | 101389286 | 3/2009 |
| CN | 101432478 A | 5/2009 |
| EP | 2022879 A1 | 2/2009 |
| EP | 2292822 A1 | 3/2011 |
| EP | 2022879 B1 | 8/2013 |
| JP | 59-157366 | 9/1984 |
| JP | 6-128853 A | 5/1994 |
| JP | 2002-20957 A | 1/2002 |
| JP | 2003-235892 A | 8/2003 |
| JP | 2003-250836 A | 9/2003 |
| JP | 2004-73759 A | 3/2004 |
| JP | 2006-043998 A | 2/2006 |
| JP | 2006-51649 A | 2/2006 |
| JP | 2006-188804 A | 7/2006 |
| JP | 2007-9403 A | 1/2007 |
| JP | 2007-138374 A | 6/2007 |
| WO | WO 00/32854 | 6/2000 |
| WO | WO 02054977 A2 | 7/2002 |
| WO | WO 02054977 A3 | 1/2003 |
| WO | WO 2007/138733 A2 | 12/2007 |
| WO | WO 2008/133067 A1 | 11/2008 |

OTHER PUBLICATIONS

Chinese Office Action dated Apr. 13, 2015 issued by the State Intellectual Property Office of People's Republic of China in corresponding Chinese Patent Application No. 201080034285.0.
Chinese Office Action dated Oct. 10, 2013, issued by the State Intellectual Property Office of People's Republic of China in corresponding Chinese Application No. 201080034285.0. (10 pgs.).
Extended European Search Report dated Aug. 9, 2013, issued by the European Patent Office in corresponding European Patent Application No. 10806342.1 (6 pgs.).
International Search Report (PCT/ISA/210) dated Sep. 28, 2010, by Japanese Patent Office as the International Searching Authority for International Application No. PCT/JP2010/062331.

[Fig. 1]
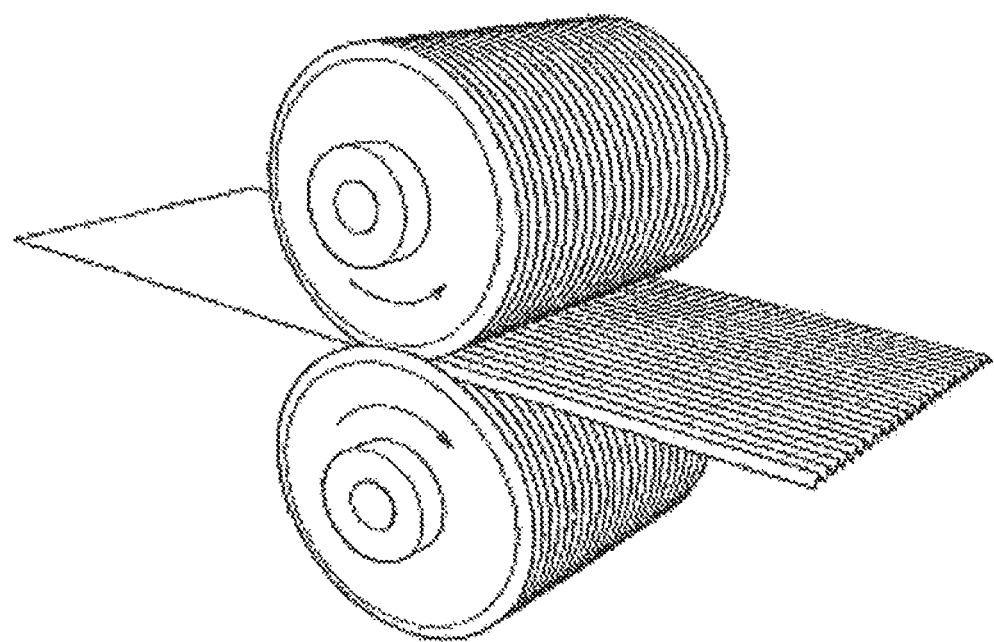
[Fig. 2]
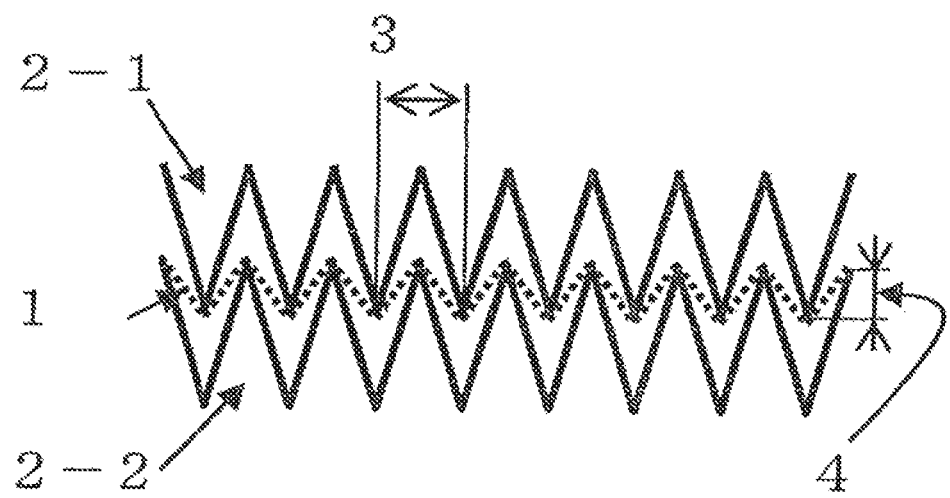

[Fig. 3]
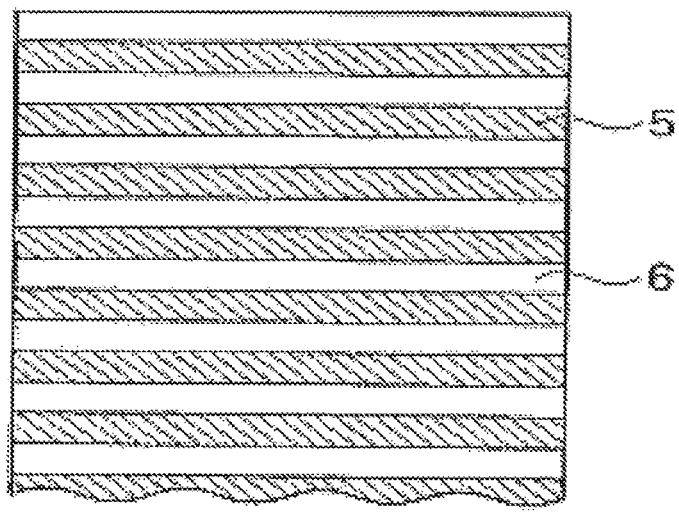
[Fig. 4]
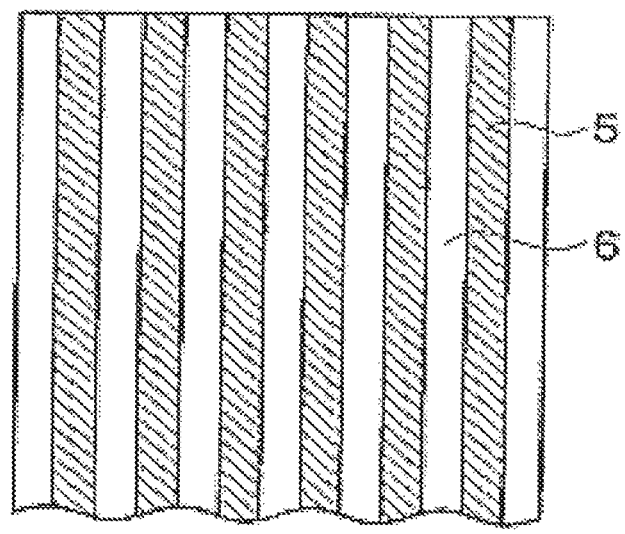

[Fig. 5]
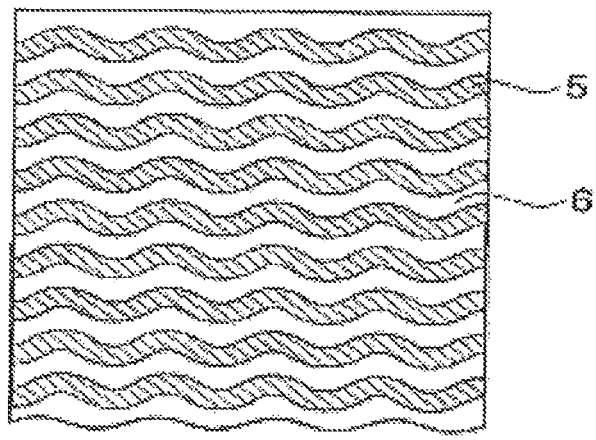
[Fig. 6]
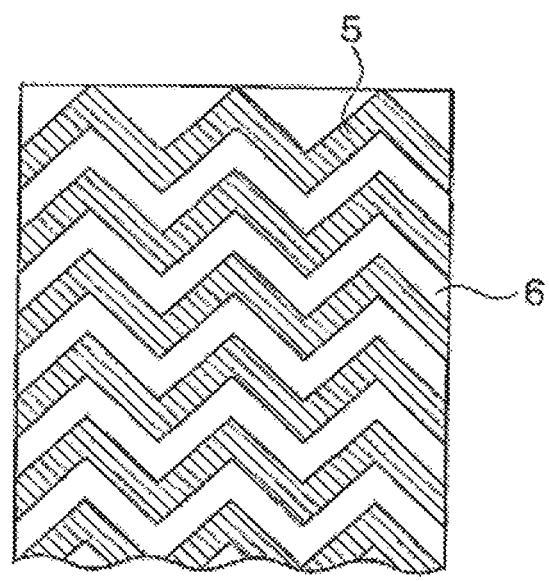

[Fig. 7]
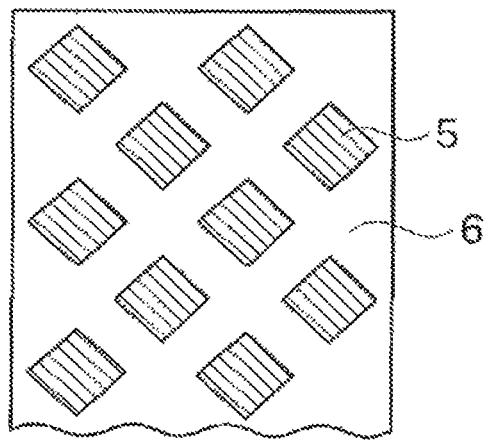
[Fig. 8]
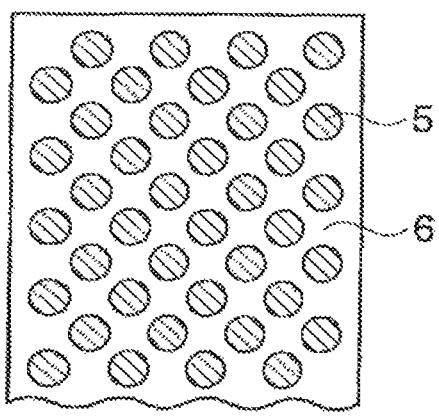
[Fig. 9]
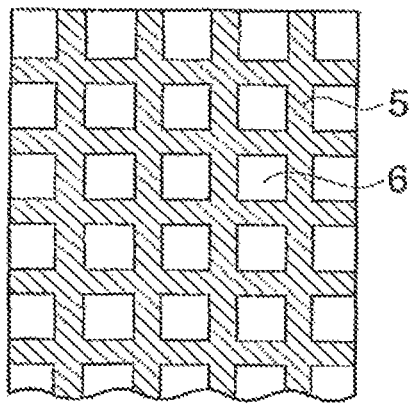

METHOD FOR PRODUCING A MIXED FIBER SPUNBONDED NONWOVEN WEB

CROSS-REFERENCES TO RELATED APPLICATIONS

This application is a divisional of U.S. application Ser. No. 13/384,721 filed on Jan. 18, 2012, now abandoned, which is a National Stage of International Application No. PCT/JP2010/062331 filed on Jul. 22, 2010, and claims priority to Japanese Application No. 2009-182673 filed on Aug. 5, 2009, and Japanese Application No. 2010-023197 filed on Feb. 4, 2010, the entire content of all four of which is incorporated herein by reference.

TECHNICAL FIELD

The present invention relates to a mixed fiber spunbonded nonwoven fabric which has high bulkiness, excellent initial hydrophilicity, long-lasting hydrophilicity, liquid dispersibility, liquid transpiration property, moisture permeability, breathability, softness, resistance to fluff, stretchability and touch, and low stickiness, and which is suitable for sheets constituting absorbent articles such as sanitary napkins, panty liners, incontinence pads, and disposable diapers, the examples of such sheets including a surface sheet, a second sheet, a sheet for lapping an absorber (core lap), and a back sheet.

TECHNICAL BACKGROUND

Since nonwoven fabrics have excellent breathability and softness, they have been widely used for surface sheets and back sheets of absorbent articles such as disposable diapers and sanitary napkins, which are required to have absorbing properties for quickly transferring liquids excreted or discharged such as blood and urine to absorbers, and surface properties for providing wearer's and handler's skins contacting with the surface with softness and low irritation.

As a method of improving the skin touch properties and wet backing properties concerning surface sheets, Patent document 1 discloses a method of laminating a high shrinkable fiber sheet with a low shrinkable or non-shrinkable nonwoven fabric and heat treating the laminate thereby shrinking the high shrinkable fiber sheet to form wrinkles on the surface. Patent document 2 discloses a method of laminating a bulky nonwoven fabric provided with bulkiness by hot air treatment with a shrink potential-having fiber nonwoven fabric capable of being shrunk by heat treatment.

Furthermore, as a method for improving absorption and transferring rate of liquids such as urine discharged, Patent document 3 discloses a method of preparing a nonwoven fabric having a complex phase structure with a low water permeating part that has a bulky layered structure of a hydrophobic fiber layer and a hydrophilic fiber layer, and a water permeating part in which a hydrophobic fiber and a hydrophilic fiber are mingled. Patent document 4 discloses a method of preparing a nonwoven fabric by mixing a hydrophilic fiber and a water repellent fiber.

The heat treatment method for providing a nonwoven fabric with bulkiness, however, has a complicated process. Furthermore, the heat treatment does not thin fibers forming the nonwoven fabric, and possibly involve heat shrinkage increasing the diameter of fibers; anyhow, the heat treatment may lead to reduced softness and touch. Further, the nonwoven fabric obtainable by mixing the hydrophilic fiber and the water repellent fiber is insufficient in liquid dispersibility, failing to provide a surface sheet simultaneously having softness and liquid dispersibility.

Patent document 5 discloses adding a nonionic surface-active agent such as polyoxyethylene alkylether in order to hydrophilize a nonwoven fabric such as a spunbonded nonwoven fabric composed of a propylene polymer. It is found, however, that by the addition of the surface-active agent, the initial hydrophilicity is improved but the long-lasting hydrophilicity is inferior. The term "initial hydrophilicity", representing such a hydrophilicity as used in a general broad sense, is optionally used in the present specification in order to be distinguished from the long-lasting hydrophilicity, which represent a hydrophilicity observed after the exposure to environment of a temperature somewhat higher than room temperature, i.e., about 40° C., for a certain period of time. In the present specification, this meaning is applied to the term. "long-lasting hydrophilicity" hereinafter.

On the other hand, the back sheet has been required to widely disperse liquids excreted or discharged such as blood, urine and sweat, and evaporate the absorbed liquids for a short period of time. As a method to realize improvement in this regard, Patent document 6, for example, proposes a method for preparing a diaper by combining a hydrophobic sheet and a hydrophilic sheet.

The method for combining the sheets, however, has a complicate process. Furthermore, since only apart of the diaper absorbs liquid, the liquid may remain within the diaper.

CITATION LIST

Patent Documents

Patent document 1: JP-A-H06-128853
Patent document 2: JP-A-2003-250836
Patent document 3: JP-A-2002-20957
Patent document 4: JP-A-2004-73759
Patent document 5: JP-A-2006-188804
Patent document 6: JP-A-2003-235892

SUMMARY OF THE INVENTION

Problem to be Solved by the Invention

It is an object of the present invention to provide a mixed fiber spunbonded nonwoven fabric which has excellent initial hydrophilicity, long-lasting hydrophilicity, liquid dispersibility, liquid transpiration property, moisture permeability, breathability, softness, resistance to fluff, stretchability and touch, and low stickiness, and which is suitable for sheets constituting absorbent articles such as sanitary napkins, panty liners, incontinence pads, and disposable diapers, the example of such sheets including a surface sheet, a second sheet, a sheet for lapping an absorber (core lap), and a back sheet.

In order to solve the problem, the present inventors have studied variously and found that the problem can be solved by pressing a spunbonded nonwoven fabric obtainable by mixing a hydrophilization-treated thermoplastic resin long fiber with a thermoplastic elastomer long fiber.

Means for Solving the Problem

The present invention provides a mixed fiber spunbonded nonwoven fabric which comprises 90 to 10% by weight of a long fiber of thermoplastic resin (A) that has been hydrophilization-treated and 10 to 90% by weight of along fiber of thermoplastic elastomer (B), wherein the mixed fiber spunbonded nonwoven fabric has a strength ratio [the ratio of a strength at 20% of an elongation at a maximum strength (elongation at a maximum point) to the maximum strength] in at least one direction of not more than 40% and a bulk density of 0.10 to 0.40 g/cm$^3$.

The present invention further provides a method for producing a mixed fiber spunbonded nonwoven fabric comprising the steps of partially heat fusing a mixed fiber spunbonded nonwoven fabric which comprises 90 to 10% by weight of a long fiber of thermoplastic resin (A) that has been hydrophilization-treated and 10 to 90% by weight of along fiber of thermoplastic elastomer (B), stretching the mixed fiber spunbonded nonwoven fabric in at least one direction and relaxing the stretched mixed fiber spunbonded nonwoven fabric, and pressing the relaxed mixed fiber spunbonded nonwoven fabric.

Effect of the Invention

The mixed fiber spunbonded nonwoven fabric of the present invention has high bulkiness, excellent initial hydrophilicity, long-lasting hydrophilicity, liquid dispersibility, liquid transpiration property, moisture permeability, breathability, softness, resistance to fluff, stretchability and touch, and low stickiness, so that it is suitable for a surface sheet, a second sheet, or a back sheet of absorbent articles.

BRIEF DESCRIPTION OF DRAWINGS

FIG. 1 is a schematic view of a gear processing machine.
FIG. 2 is a pattern diagram of gears of a gear processing machine and a mixed fiber spunbonded nonwoven fabric to be gear-processed.
FIG. 3 is a plane schematic view of a partially pressed mixed fiber spunbonded nonwoven fabric.
FIG. 4 is a plane schematic view of a partially pressed mixed fiber spunbonded nonwoven fabric.
FIG. 5 is a plane schematic view of a partially pressed mixed fiber spunbonded nonwoven fabric.
FIG. 6 is a plane schematic view of a partially pressed mixed fiber spunbonded nonwoven fabric.
FIG. 7 is a plane schematic view of a partially pressed mixed fiber spunbonded nonwoven fabric.
FIG. 8 is a plane schematic view of a partially pressed mixed fiber spunbonded nonwoven fabric.
FIG. 9 is a plane schematic view of a partially pressed mixed fiber spunbonded nonwoven fabric.

EMBODIMENT FOR CARRYING OUT THE INVENTION

<Thermoplastic Resin (A)>

As a thermoplastic resin (A), which is one of the components forming the mixed fiber spunbonded nonwoven fabric of the present invention and which serves as a raw material of the thermoplastic resin long fiber, various known thermoplastic resins can be used. The thermoplastic resin (A) is a resinous polymer different from a thermoplastic elastomer (B) as described later and is usually a crystalline polymer having a melting point (Tm) of not lower than 100° C. or a non-crystalline polymer having a glass transition temperature of not lower than 100° C. Among these thermoplastic resins (A), the crystalline thermoplastic resin is preferred.

Moreover, among the thermoplastic resins (A), it is preferred to use such a thermoplastic resin (extensible thermoplastic resin) that forms a nonwoven fabric obtained by a known spunbonded nonwoven fabric production method which has an elongation at the maximum point of not less than 50%, preferably not less than 70%, more preferably not less than 100%, and which has quite low elastic recovery. When such an extensible thermoplastic resin is mixed with the long fiber of thermoplastic elastomer (B) to produce a mixed fiber spunbonded nonwoven fabric intended for the use in e.g., a surface sheet, and then the mixed fiber spunbonded nonwoven fabric is stretch-processed thereby stretching the long fiber of extensible thermoplastic resin and the long fiber of thermoplastic elastomer (B) followed by releasing the stress, only the long fiber of thermoplastic elastomer (B) shows elastic recovery, while the long fiber of extensible thermoplastic resin elongated is folded without elastic recovery. As a result, the mixed fiber spunbonded nonwoven fabric exhibits bulkiness, and moreover the long fiber of extensible thermoplastic resin is made thinner by elongation to have improved softness and touch and an elongation-suppressing property. The upper limit of the elongation at the maximum point of the spunbonded nonwoven fabric composed of the thermoplastic resin (A), which is not particularly limited, is usually not more than 300%.

Examples of the thermoplastic resin (A) are polyolefins which are homopolymers or copolymers of α-olefins including ethylene, propylene, 1-butene, 1-hexene, 4-methyl-1-pentene, 1-octene and the like, the polyolefins including ethylene polymers, e.g., high pressure low density polyethylene, linear low density polyethylene (namely, LLDPE), high density polyethylene (namely, HDPE), and propylene polymers, e.g., polypropylene (propylene homopolymer) and polypropylene random copolymer, the polyolefins further including poly-1-butene, poly-4-methyl-1-pentene, ethylene/propylene random copolymer, ethylene/1-butene random copolymer, and propylene/1-butene random copolymer. Further examples of the thermoplastic resin (A) include polyesters such as polyethylene terephthalate, polybutylene terephthalate, and polyethylene naphthalate, polyamides such as nylon-6, nylon-66, and polymethaxylene adipamide, polyvinyl chloride, polyimide, ethylene/vinyl acetate copolymer, ethylene/vinyl acetate/vinyl alcohol copolymer, ethylene/(meth)acrylic acid copolymer, ethylene/acrylic acid ester/carbon monoxide copolymer, polyacrylonitrile, polycarbonate, polystyrene, ionomer and mixtures thereof. Of these, ethylene polymers such as high-pressure low density polyethylene, linear low density polyethylene (namely, LLDPE), high density polyethylene, propylene polymers such as polypropylene and polypropylene random copolymer, polyethylene terephthalate and polyamides are more preferred.

Of these thermoplastic resins (A), propylene polymers are particularly preferred in view of spinning stability at molding or stretching processability of a nonwoven fabric.

Preferable examples of the propylene polymer are a propylene homopolymer and copolymer having a melting point (Tm) of not lower than 135° C., the copolymer being composed of propylene and not more than 10 mol % of one or two or more α-olefins having 2 or more carbon atoms (excluding 3 carbon atoms), preferably 2 to 8 carbon atoms (excluding 3 carbon atoms), such as ethylene, 1-butene, 1-pentene, 1-hexene, 1-octene, and 4-methyl-1-pentene.

Of these propylene polymers, preferred is a propylene/α-olefin random copolymer having a melting point of 135 to 155° C., because a mixed fiber spunbonded nonwoven fabrics having excellent properties such as stretchability, initial hydrophilicity, long-lasting hydrophilicity, softness and touch can be prepared.

The melt flow rate (MFR: ASTMD-1238, 230° C. under a load of 2160 g) of the propylene polymer is not particularly limited as long as melt spinning thereof can be carried out. The melt flow rate is usually 1 to 1000 g/10 min, preferably 5 to 500 g/10 min, more preferably 10 to 100 g/10 min. Furthermore, in the propylene polymer of the present invention, the ratio of weight average molecular weight (Mw) to number average molecular weight (Mn) (Mw/Mn) is usually 1.5 to 5.0. The ratio is further preferably 1.5 to 3.0 because the spinning properties are good and fibers having particularly excellent fiber strength can be prepared. Mw and Mn can be determined using GPC (Gel permeation chromatography) by a known method.

In view of spinning properties and stretching processability, preferred is an olefin polymer composition obtainable by adding a small amount, preferably 1 to 20% by weight, more preferably 2 to 15% by weight, still more preferably 4 to 10% by weight of a high density polyethylene (HDPE) to the propylene polymer, wherein the total amount of the propylene polymer and HDPE is 100% by weight, because a nonwoven fabric laminate having more improved stretching processability can be prepared.

The HDPE to be added to the propylene polymer has a density, which is not particularly limited, of usually 0.94 to 0.97 g/cm$^3$, preferably 0.95 to 0.97 g/cm$^3$, more preferably 0.96 to 0.97 g/cm$^3$. The HDPE has a melt flow rate (MFR: ASTMD-1238, 190° C. under a load of 2160 g), which is not particularly limited as long as it has spinnability, of usually 0.1 to 100 g/10 min, more preferably 0.5 to 50 g/10 min, furthermore preferably 1 to 30 g/10 min in view of exhibition of extensibility. In the present invention, the term "good spinnability" indicates the fact that fiber breakage is not caused at the time of outputting fiber from a spinning nozzle and during stretching, and filament fusing is not caused.

<Thermoplastic Elastomer (B)>

As the thermoplastic elastomer (B), which is one of the components forming the mixed fiber spunbonded nonwoven fabric of the present invention, various known thermoplastic elastomers can be used, and two or more thermoplastic elastomers may be used in combination. Specific examples thereof are:

styrene elastomers comprising block copolymers obtainable by at least one polymer block composed of aromatic vinyl compound such as styrene and at least one polymer block composed of conjugated diene compound such as butadiene and isoprene, or hydrogenated products of the block copolymer, which are typified by polystyrene-polybutadiene-polystyrene block copolymer (referred to SBS), polystyrene-polyisoprene-polystyrene block copolymer (referred to SIS), and their hydrogenated products, e.g., polystyrene-poly/ethylene/butylene-polystyrene block copolymer (referred to SEBS) and polystyrene-poly/ethylene/propylene-polystyrene block copolymer (referred to SEPS);

polyester elastomers typified by a block copolymer composed of a high crystalline aromatic polyester and a non-crystalline aliphatic polyether;

polyamide elastomers typified by a block copolymer composed of a crystalline polyamide having a high melting point and a non-crystalline polyether or polyester having a low glass transition temperature (Tg);

thermoplastic polyurethane elastomers typified by a block copolymer composed of as a hard segment a polyurethane and as a soft segment a polycarbonate polyol, an ether polyol, a caprolactone polyester or an adipate polyester;

polyolefin elastomers typified by a non-crystalline or low-crystalline random copolymer, e.g., an ethylene/α-olefin random copolymer, a propylene/α-olefin random copolymer or a propylene/ethylene/α-olefin random copolymer, or a mixture of the non-crystalline or low-crystalline random copolymer with a crystalline polyolefin, e.g., a propylene homopolymer, a copolymer of propylene and a small amount of an α-olefin, high density polyethylene, and middle density polyethylene;

polyvinyl chloride elastomers; and fluorine elastomers.

Examples of the styrene elastomers are diblock and triblock copolymers obtainable by using, as a base, polystyrene block and butadiene rubber block or isoprene rubber block. The rubber block may be unsaturated or hydrogenated completely. Examples of the styrene elastomer are KRATON POLYMER (product name, manufactured by Schell Chemicals Ltd.), SEPTON (product name, manufactured by Kuraray Co. Ltd.), TUFTEC (product name, manufactured by Asahi Kasei Co.) and LEOSTOMER (product name, manufactured by Riken technos. Co.).

Examples of the polyester elastomer are HYTREL (product name, manufactured by E. I. Dupont Co.) and PELPRENE (product name, manufactured by TOYOBO. CO., Ltd.).

An example of the polyamide elastomer is PEBAX (product name, manufactured by Atofina Japan).

Examples of the polyolefin elastomer are an ethylene/α-olefin copolymer and a propylene/α-olefin copolymer. Specific examples thereof are TAFMER (product name, manufactured by Mitsui Chemicals Inc.), NOTIO (product name, manufactured by Mitsui Chemicals Inc.), VISTMAXX (product name, manufactured by Exxon Mobil Inc.), Engage, which is an ethylene-octene copolymer (product name, manufactured by DuPont Dow Elastomers Inc.) and CATALLOY containing a crystalline olefin copolymer (product name, manufactured by Montel Inc.).

Examples of the polyvinyl chloride elastomer are Leonyl (product name, manufactured by Riken Technos Co.) and Posmile (product name, manufactured by Shin-Etsu Polymer Co., Ltd.).

Of these thermoplastic elastomers (B), the polyolefin elastomer and thermoplastic polyurethane elastomer are preferred. Particularly, the thermoplastic polyurethane elastomer is preferred because of having stretchability, processability and moisture permeability and being capable of preparing a mixed fiber spunbonded nonwoven fabric having excellent initial hydrophilicity and long-lasting hydrophilicity.

<Thermoplastic Polyurethane Elastomer>

Of the thermoplastic polyurethane elastomers, thermoplastic polyurethane elastomers having a starting temperature for solidification of not lower than 65° C., preferably not lower than 75° C., most preferably not lower than 85° C. are preferred. The upper limit of the starting temperature for solidification is preferably 195° C. The starting temperature for solidification is measured by a differential scanning calorimeter (DSC) and determined in such a way that the temperature of the thermoplastic polyurethane elastomer is increased at a rate of 10° C./min to 230° C. and kept at 230° C. for 5 min, and then when the temperature thereof is decreased at a rate of 10° C./min, the temperature at which an exothermic peak derived from the solidification of the resulting thermoplastic polyurethane elastomer is started is taken as the starting temperature for solidification. When the starting temperature for solidification is not lower than 65° C., it is possible to prevent defective molding such as fusion of fibers, broken fiber, massed resin in preparing mixed fiber spunbonded nonwoven fabrics, and also it is possible to prevent mixed fiber spunbonded nonwoven fabrics from winding to an emboss roller in thermal emboss processing. Furthermore, the resulting mixed fiber spunbonded nonwoven fabrics have low stickiness and are suitably used for materials contacting with skin such as clothes, hygienic materials, and materials of sporting goods. On the other hand, when the starting temperature for solidification is not higher than 195° C., it is possible to improve the molding processability. The starting temperature for solidification of the molded fiber tends to be higher than that of the thermoplastic polyurethane elastomer used for the molded fiber.

In order to regulate the starting temperature for solidification of the thermoplastic polyurethane elastomer so as to be not lower than 65° C., it is necessary to select a polyol, an isocyanate compound and a chain extender each having an optimum chemical structure, which are used as raw materials for the thermoplastic polyurethane elastomer, and to regulate the amount of a hard segment. The amount of the hard segment is a value (% by weight) determined by dividing the total weight of the isocyanate compound and the chain extender which are used in the preparation of the thermoplastic polyurethane elastomer by the total weight of the polyol, the isocyanate compound and the chain extender and multiplying the resulting value by 100. The hard segment amount is preferably 20 to 60% by weight, more preferably 22 to 50% by weight, most preferably 25 to 48% by weight.

The thermoplastic polyurethane elastomer has a particle number of components insoluble in a dimethyl acetoamide (hereinafter referred to "DMAC") solvent of preferably not more than 3,000,000 particles/g, more preferably not more than 2,500,000 particles/g, still more preferably not more than 2,000,000 particles/g. In the thermoplastic polyurethane elastomer, the components insoluble in the DMAC solvent are mainly agglomerates such as fish eye and gel generated during the production of the thermoplastic polyurethane elastomer. The agglomerates are components caused by the raw materials constituting the thermoplastic polyurethane elastomer and by chemical reaction between these raw materials, the components being, for example, those derived from hard segment agglomerates of the thermoplastic polyurethane elastomer and those obtainable by crosslinking the hard segment and/or the soft segment with allophanate bond or biuret bond.

The particle number of the components insoluble in the DMAC solvent is determined by dissolving the thermoplastic polyurethane elastomer in DMAC and measuring the insoluble components by means of a particle size distribution measuring apparatus equipped with a 100 µm aperture utilizing an electrical sensing zone method. Using the apparatus equipped with a 100 µm aperture, the number of particles of 2 to 60 mm can be measured in terms of uncrosslinked polystyrene.

By regulating the particle number of the components insoluble in the DMAC solvent so as to be not more than 3,000,000 per 1 g of the thermoplastic polyurethane elastomer, it is possible to more prevent problems in the starting temperature range for solidification of the thermoplastic polyurethane elastomer, the problems including increase in a distribution of a fiber diameter, and fiber breakage in spinning. Moreover, in the molding of nonwoven fabrics using a large-size spunbonding molding machine, in view of preventing mingling of bubbles into a strand or occurrence of fiber breakage, the thermoplastic polyurethane elastomer has a water content of preferably not more than 350 ppm, more preferably not more than 300 ppm, most preferably not more than 150 ppm.

In the thermoplastic polyurethane elastomer, in view of stretchability, the total sum (a) of heat of fusion determined from the endothermic peaks at a peak temperature of 90 to 140° C. and the total sum (b) of heat of fusion determined from the endothermic peaks at a peak temperature of over 140° C. and not higher than 220° C., as measured by a differential scanning calorimeter, preferably satisfy the following formula (I);

$$a/(a+b) \leq 0.8 \qquad (I),$$

more preferably the following formula (II);

$$a/(a+b) \leq 0.7 \qquad (II),$$

still more preferably the following formula (III);

$$a/(a+b) \leq 0.55 \qquad (III).$$

The ratio of a/(a+b) means a ratio (unit: %) of heat of fusion of the hard domain of the thermoplastic polyurethane elastomer. When the ratio of heat of fusion of the hard domain of the thermoplastic polyurethane elastomer is not more than 80%, fibers, particularly fibers and nonwoven fabric in mixed fiber spunbonded nonwoven fabrics, have improved strength and stretchability. In the present invention, the lower limit of the ratio of heat of fusion of the hard domain of the thermoplastic polyurethane elastomer is preferably about 0.1%.

The thermoplastic polyurethane elastomer has a melt viscosity, as measured at 200° C. at a shear rate of 100 sec$^{-1}$ of preferably 100 to 3000 Pa·s, more preferably 200 to 2000 Pa·s, most preferably 1000 to 1500 Pa·s. The melt viscosity is determined by a capirograph (manufactured by Toyo Seiki Co., Ltd., a nozzle length of 30 mm, a diameter of 1 mm).

The thermoplastic polyurethane elastomer having such properties can be obtained by, for example, the production process as described in JP-A-2004-244791.

The thermoplastic polyurethane elastomer having a low content of the components insoluble in the DMAC solvent is obtainable by polymerization-reacting the polyol, the isocyanate compound and the chain extender, followed by filtration, as described later.

<Hydrophilization Treatment Agent (Hydrophilizing Agent)>

In order provide the mixed fiber spunbonded nonwoven fabric according to the present invention with the initial hydrophilicity and the long-lasting hydrophilicity, at least the long fiber of thermoplastic resin (A) needs to be provided with hydrophilicity. Examples of the hydrophilization treatment agent for providing the hydrophilicity are surface-active agents, and a nonionic surface-active agent is preferred among them. Examples of the nonionic surface-active agent are ether type nonionic surface-active agents such as polyoxyethylene alkylether, polyoxypropylene alkylether, polyoxyethylene alkylphenylether or polyoxypropylene alkylphenylether; polyhydric alcohol ether type nonionic surface-active agents such as alkyl glycoxide; ester type nonionic surface-active agents such as polyoxyethylene aliphatic acid ester or polyoxypropylene aliphatic acid ester; polyhydric alcohol ester type nonionic surface-active agents such as sucrose aliphatic acid ester, sorbitane aliphatic acid ester, polyoxyethylene aliphatic acid ester or polyoxypropylene aliphatic acid ester; and amide type nonionic surface-active agents such as aliphatic acid alkanolamide or alkylene oxide adducts of an aliphatic amide having an acyl group of 8 to 18 carbon atoms.

These nonionic surface-active agents may be used singly or as a mixture of two or more of the nonionic surface-active agents.

As the ether type nonionic surface-active agents, surface-active agents having an alkyl group of 8 to 50 carbon atoms or an alkylphenyl group with an alkyl group of 8 to 18 carbon atoms are preferred.

Of these nonionic surface-active agents, ether type nonionic surface-active agents made from an alkylene oxide adduct of an aliphatic alcohol having 10 to 40 carbon atoms, preferably 12 to 24 carbon atoms, more preferably 16 to 22 carbon atoms (AE type nonionic surface-active agents) and ester type nonionic surface-active agents having an ester of an aliphatic acid of 8 to 18 carbon atoms are preferred.

As a method for hydrophilization-treating the long fiber of the thermoplastic resin (A), the addition of the hydrophilization treatment agent can mentioned, with specific methods thereof including the application of the hydrophilization treatment agent to the long fiber, and the addition of the hydrophilization treatment agent to the thermoplastic resin (A) followed by fiberization (kneading). As a particularly preferred method, 0.1 to 10 parts by weight, more preferably 0.5 to 7 parts by weight of the nonionic surface-active agent as the hydrophilization treatment agent is applied onto the surfaces of the long fiber of the thermoplastic resin (A), or is kneaded into the thermoplastic resin (A), based on 100 parts by weight of the thermoplastic resin (A). Moreover, in view of long-lasting hydrophilicity, more preferred is the addition of the hydrophilization treatment agent to the thermoplastic resin (A) followed by fiberization (kneading).

When the addition amount of the hydrophilization treatment agent is less than 0.1 part by weight, the resulting mixed fiber spunbonded nonwoven fabrics may have insufficiently improved initial hydrophilicity and long-lasting hydrophilicity. On the other hand, the amount exceeding 10 parts by weight may lead to decreased processability and increased amount of the hydrophilization treatment agent being soaked on the fiber surface resulting in a sticky mixed fiber spunbonded nonwoven fabric.

Since the mixed fiber spunbonded nonwoven fabrics having excellent long-lasting hydrophilicity can retain good hydrophilicity even after being kept at high temperatures or heat processing in the production of absorbent goods, they are preferably used for applications including a surface sheet, a second sheet, a sheet for lapping an absorber (core lap), or a back sheet of absorbent articles such as sanitary napkins, panty liners, incontinence pads and disposable diapers.

<Other Additives>

In the present invention, to the mixed fiber spunbonded nonwoven fabrics, it is possible to add, as an optional component, various stabilizers such as a heat stabilizer and a weather stabilizer, a slipping agent, an antifogging agent, a lubricant, a dye, a pigment, a natural oil, a synthetic oil and a wax.

Examples of the stabilizers are an anti-oxidant such as 2,6-di-t-butyl-4-methylphenol (BHT); a phenol anti-oxidant such as tetrakis[methylene-3-(3,5-di-t-butyl-4-hydroxyphenyl)propionate]methane, 6-(3,5-di-t-butyl-4-hydroxyphenyl)propionic acid alkyl ester, 2,2'-oxamidobis[ethyl-3-(3,5-di-t-butyl-4-hydroxy phenyl)]propionate, and Irganox 1010 (hindered phenol anti-oxidant: product name); and an aliphatic acid metal salt such as zinc stearate, calcium stearate, and calcium 1,2-hydroxystearate.

These may be used singly or two or more may be combined for use.

<Mixed Fiber Spunbonded Nonwoven Fabric>

The mixed fiber spunbonded nonwoven fabric of the present invention is a mixed fiber spunbonded nonwoven fabric which comprises 90 to 10% by weight of the long fiber of thermoplastic resin (A) that has been hydrophilization-treated and 10 to 90% by weight of the long fiber of thermoplastic elastomer (B), wherein the mixed fiber spunbonded nonwoven fabric has a strength ratio [the ratio of a strength at 20% of an elongation at a maximum strength (elongation at a maximum point) to the maximum strength] in at least one direction of not more than 40%, preferably not more than 30%, and a bulk density of 0.10 to 0.40 g/cm$^3$, preferably 0.11 to 0.35 g/cm$^3$.

The mixed fiber spunbonded nonwoven fabric of the present invention has a strength ratio in at least one direction of not more than 40% and a bulk density of 0.10 to 0.40 g/cm$^3$, thereby having excellent stretchability, liquid dispersibility, liquid transpiration property. A mixed fiber spunbonded nonwoven fabric not having a strength ratio and bulk density within the above range may have inferior stretchability, liquid dispersibility, liquid transpiration property.

The mixed fiber spunbonded nonwoven fabric of the present invention has a liquid dispersion area of not less than 60 cm$^2$, or 65 to 200 cm$^2$, and a liquid evaporation time of not more than 180 minutes, or not more than 100 minutes, or 65 to 5 minutes.

The mixed fiber spunbonded nonwoven fabric of the present invention has a breathability of preferably not less than 40 cm$^3$/cm$^2$/sec, more preferably not less than 50 to 420 cm$^3$/cm$^2$/sec.

The mixed fiber spunbonded nonwoven fabric having a strength ratio and a bulk density within the above range is obtained by preparing a web, which is a precursor of a mixed fiber spunbonded nonwoven fabric and which comprises 90 to 10% by weight of the long fiber of thermoplastic resin (A) that has been hydrophilization-treated and 10 to 90% by weight of the long fiber of thermoplastic elastomer (B), stretching the web in at least one direction and relaxing the stretched web, and pressing the relaxed web.

In the mixed fiber spunbonded nonwoven fabric of the present invention, its entire surface may be pressed, or its partial surface may be pressed.

The mixed fiber spunbonded nonwoven fabric of the present invention having a larger pressed area can have a larger liquid dispersion area and a shorter liquid evaporation time, but has a lower breathability.

Thus, in accordance with uses of the mixed fiber spunbonded nonwoven fabric, the pressed area of the mixed fiber spunbonded nonwoven fabric is selected, thereby controlling the liquid dispersion time, the evaporation time and the breathability. When the pressed area is small, however, the liquid dispersion area is small, and the liquid evaporation time is long. In view of this, usually at least 20%, preferably 25% of the area of the mixed fiber spunbonded nonwoven fabric has been pressed.

The shape of the pressed portion of the partially pressed mixed fiber spunbonded nonwoven fabric is not particularly limited, and various shapes may be adopted, with examples thereof including linear shape (stripe shape) as shown in FIGS. 3 and 4, a wavy line shape as shown in FIG. 5, a zigzag shape as shown in FIG. 6, an island shape (dot shape) as shown in FIG. 7, a circle shape, a ring shape and an oval shape as shown in FIG. 8, a grid shape and a check shape as shown in FIG. 9, and preferred designs, e.g., a floral design, an animal design and a character design.

By increasing the pressed area of the mixed fiber spunbonded nonwoven fabric of the present invention, the liquid dispersion time can be controlled to be not less than 60 cm$^2$, or 65 to 200 cm$^2$; and the liquid evaporation time can be controlled be not more than 180 minutes, or not more than 100 minutes, or 65 to 5 minutes.

The mixed fiber spunbonded nonwoven fabric of the present invention having a larger pressed area has a lower breathability. When the pressed area is 100%, for example, the breathability needs controlling to be at least 40 cm$^3$/cm$^2$/sec, although depending on other factors such as stretch treatment and press temperature. Controlling of the breathability so as to be 120 to 420 cm$^3$/cm$^2$/sec can be achieved by controlling the pressed area so as to be around 75% to 25%.

By pressing, preferably, the long fiber of thermoplastic resin (A) that has been hydrophilization-treated and/or the long fiber of thermoplastic elastomer (B) contained in the mixed fiber spunbonded nonwoven fabric have a partially fused surface.

The mixed fiber spunbonded nonwoven fabric of the present invention may be a single layer nonwoven fabric, or may be a multi-layer nonwoven fabric having two or more layers.

When the nonwoven fabric is a multi-layer nonwoven fabric having two or more layers, as long as the multi-layer nonwoven fabric has the long fiber of thermoplastic resin (A) that has been hydrophilization-treated and the long fiber of thermoplastic elastomer (B) within the above amount ranges, the individual nonwoven fabrics therein may the same as or different from each other in terms of the mixing ratio in each nonwoven fabric, or the individual nonwoven fabrics therein may be different from each other in terms of the basis weight, the fiber diameter, the addition amount of the hydrophilizing agent, and the like.

In the case of the multi-layer nonwoven fabric having two or more layers, the individual layers may be stretched and/or pressed before they are laminated; or the individual layers may be laminated and then, the laminate is stretched and/or pressed. Further, only any one layer may be stretched and/or pressed. At this time, by using the pressed layer so as to contact with skin, more satisfactory liquid dispersibility and liquid transpiration property can be obtained.

By pressing, the pressed nonwoven fabric, i.e., the mixed fiber spunbonded nonwoven fabric of the present invention, can be provided with good liquid dispersibility and liquid transpiration property, but has a lower breathability. As mentioned above, partially pressing a stretched precursor of the mixed fiber spunbonded nonwoven fabric can increase the breathability. But, the breathability can be increased also by laminating a web (a precursor of the mixed fiber spunbonded nonwoven fabric) which has not yet press-treated on one surface or both surfaces entirely-pressed or almost entirely-pressed of the mixed fiber spunbonded nonwoven fabric, and stretching the laminate preferably at a ratio of 1.5 to 10. By this method, too, the breathability can be controlled to be 120 to 420 cm$^3$/cm$^2$/sec.

The long fiber of thermoplastic resin (A) forming the mixed fiber spunbonded nonwoven fabric of the present invention needs to be hydrophilization-treated, but the long fiber of thermoplastic elastomer (B) may be not hydrophilization-treated.

The mixed fiber spunbonded nonwoven fabric comprises the long fiber of thermoplastic elastomer (B) in an amount of preferably not less than 20% by weight, more preferably not less than 30% by weight in view of stretchability, softness, initial hydrophilicity and long-lasting hydrophilicity, and in an amount of preferably not more than 80% by weight, more preferably not more than 70% by weight in view of processability (resistance to stickiness).

In the mixed fiber spunbonded nonwoven fabric of the present invention, the fiber diameter (average value) of the long fiber of thermoplastic resin (A) and that of the long fiber of thermoplastic elastomer (B) are each usually not more than 50 μm, preferably not more than 40 μm, more preferably not more than 30 μm. The fiber diameter of the long fiber of thermoplastic resin (A) and that of the long fiber of thermoplastic elastomer (B) may be the same as or different from each other.

The mixed fiber spunbonded nonwoven fabrics of the present invention can be appropriately selected in accordance with uses. For example, when it is used as a surface material sheet of a sanitary napkin, the basis weight is usually not more than 150 g/m$^2$, preferably 15 to 120 g/m$^2$, more preferably 15 to 90 g/m$^2$, in view of softness.

<Method for Producing Mixed Fiber Spunbonded Nonwoven Fabric>

A method for producing the mixed fiber spunbonded nonwoven fabric of the present invention comprises the steps of partially heat fusing a web which comprises 90 to 10% by weight of the long fiber of thermoplastic resin (A) that has been hydrophilization-treated and 10 to 90% by weight of the long fiber of thermoplastic elastomer (B), stretching the web in at least one direction and relaxing the stretched web, and pressing the relaxed web.

When the relaxed web is pressed, an entire surface of the web may be pressed, or part of the surface of the web may be pressed. When part of the web is pressed, various known patterns can be provided by the pressing, as mentioned above.

The mixed fiber spunbonded nonwoven fabric of the present invention is obtainable by using the thermoplastic resin (A) that has been hydrophilization-treated and the thermoplastic elastomer (B) by a known method for producing spunbonded nonwoven fabrics, for example, the method as described in JP-A-2004-244791.

Specifically, the thermoplastic resin (A) that has been hydrophilization-treated and the thermoplastic elastomer (B) are each molten in a separate extruder, and then the molten polymers are each individually introduced into a die having a number of spinning holes (nozzles), and the thermoplastic resin (A) and the thermoplastic elastomer (B) are independently output from the individual nozzles simultaneously. Thereafter, the long fiber of the thermoplastic resin (A) and the long fiber of the thermoplastic elastomer (B) are introduced into a cooling room and cooled by cooling air, and then they are stretched (extended) by stretching air and deposited on a moving collecting surface, thereby obtaining a web. The web is partially heat fused, and the resultant web is stretched in at least one direction and then, the stretched web is relaxed. Then, the relaxed web is pressed. Thereby, the mixed fiber spunbonded nonwoven fabric of the present invention can be obtained. The cross-sectional shape of the nozzle is selectable from various known cross-sectional shapes such as circle shape, elliptical shape, cross shape and Y-shape.

The melting temperature of each polymer is not particularly limited as long as being not lower than the softening temperature or melting temperature and lower than the pyrolysis temperature of each polymer, and is determined by a polymer to be used. The die temperature, depending on a polymer to be used, is set to be usually 180 to 240° C., preferably 190 to 230° C., more preferably 200 to 225° C., for example, when the thermoplastic resin (A) that has been hydrophilization-treated is a propylene polymer or an olefin polymer composition of the propylene polymer and HDPE, and the thermoplastic elastomer (B) is a thermoplastic polyurethane elastomer or an olefin copolymer elastomer.

The temperature of the cooling air is not particularly limited as long as the polymer is solidified, but is generally 5 to 50° C., preferably 10 to 40° C., more preferably 15 to 30° C. The rate of the stretching air is usually 100 to 10,000 m/min, preferably 500 to 10,000 m/min.

Then, the deposited web is partially heat fused before stretched, but may be solidified by means of a nip roll before heat fused.

As a method for partially heat fusing the deposited web, various known methods can be mentioned as pre-bonding, such as a method of using ultrasonic wave and the like, thermal emboss processing using an embossing roll, or hot air through, but the thermal emboss processing is preferable because this method can efficiently stretch the long fibers.

When the web is partially heat fused by thermal emboss processing, the embossed area ratio is usually 5 to 20%, preferably 5 to 10%, and the un-embossed unit area is not less than 0.5 mm$^2$, preferably 4 to 40 mm$^2$. The non-embossed unit area is the largest square area surrounded by embosses in the smallest unit of the non-embossed parts surrounded by the embossed parts. Examples of the embossed shape include circle, oval, ellipse, square, lozenge, rectangle, quadrilateral and continuances of the above shapes. By having such an embossed part in the above range, the embossed part, which substantially bonds the long fiber of the thermoplastic resin (A) and the long fiber of the thermoplastic elastomer (B) constituting the web, forms a bonding point; and furthermore, the long fiber of thermoplastic elastomer (B) having elasticity and the long fiber of the (extensible fiber) thermoplastic resin (A) having elasticity substantially lower than that of the long fiber of thermoplastic elastomer (B) are present between the embosses in a high degree of freedom. As a result, the web with such a structure has decreased residual strain and is provided with good stretchability.

A larger embossed area ratio decreases a stretchable range but improves the stress. A smaller embossed area ratio can increase a stretchable range, but the increase in embossing pitch tends to somewhat increase the residual strain.

Subsequently, the partially heat fused web is stretched in at least one direction, and the stretched web is relaxed. By relaxing the web after stretching, the stretched long fiber of thermoplastic elastomer (B) has a length near the length before the stretching by elastic recovery, while the long fiber of thermoplastic resin (A) almost keeps the stretched length. Consequently, the long fiber of thermoplastic resin (A) is more folded than the long fiber of thermoplastic elastomer (B). Thus, pressing such a web, preferably 20% or more of the area thereof enables a mixed fiber spunbonded nonwoven fabric to have a high bulkiness, i.e., a bulk density of 0.10 to 0.40 g/cm$^3$, and to have excellent liquid dispersibility and liquid transpiration property. Moreover, increasing or decreasing the pressed area can control the balance among the breathability, liquid dispersibility and liquid transpiration property.

As a method to stretch the partially heat fused web in at least one direction, various known methods can be adopted. By gear-stretching specifically in accordance with the method as described in JP-A-2003-73967, the web is stretched in a longitudinal direction or in a transversal direction, usually at a ratio of 1.5 to 10, preferably a ratio of 2 to 8. By stretching the web, the strength ratio in the stretched direction can be controlled to be not more than 40%.

When the gear stretching is carried out, the stretching is carried out usually in the range of from 10 to less than 100° C., preferably in the range of from 20 to less than 80° C. Because stretching can involve the generation of heat, stretching may be carried out while cooling the gear, as needed.

The stretched web is relaxed, and then pressed, thereby providing the mixed fiber spunbonded nonwoven fabric.

In the present invention, pressing is a method different from the thermal emboss processing. Specifically, the thermal emboss processing is a method for fusing the fibers constituting the nonwoven fabric in order for the nonwoven fabric to have increased strength, and by this method, the thermal embossed portion has almost no breathability. By contrast, the pressing is intended in the present invention as a method to provide good liquid dispersibility and liquid transpiration property. By this method, the breathability of the pressed portion is rendered lower than that of a non-pressed portion, but needs to be kept at not lower than 40 cm$^3$/cm$^2$/sec.

As a method for pressing the web, various known methods can be adopted as long as the breathability is not lower than 40 cm$^3$/cm$^2$/sec. In particular, making the web go through pressurized and heated rolls enables the web to be continuously pressed, and by controlling the heating temperature so as to be a melting point of the long fiber of thermoplastic resin (A)–100° C. through a melting point of the long fiber of thermoplastic resin (A)–10° C., preferably a melting point of the long fiber of thermoplastic resin (A)–70° C. through a melting point of the long fiber of thermoplastic resin (A)–20° C., and controlling the pressurized pressure (linear pressure) so as to be 20 N/cm or higher, preferably 25 to 90 N/cm or higher, the bulk density can be controlled to be 0.10 to 0.40 g/cm$^3$. If the heating temperature and the linear pressure exceed the aforementioned ranges, the breathability may be lower than 40 cm$^3$/cm$^2$/sec.

The mixed fiber spunbonded nonwoven fabric of the present invention may be laminated with other layers in accordance with various uses. The other layers to be laminated with the mixed fiber spunbonded nonwoven fabric of the present invention are not particularly limited and various layers can be laminated in accordance with the uses.

Specific examples of the other layers include knit fabrics, woven fabrics, nonwoven fabrics and films. When the mixed fiber spunbonded nonwoven fabric of the present invention is further laminated (adhered) with other layers, it is possible to employ various known methods such as heat fusion methods including thermal emboss processing and ultrasonic fusion; mechanical co-founding methods including needle punch and water jet; and methods of using adhesives such as hot melt adhesive and urethane type adhesive; and extrusion laminating.

Examples of the nonwoven fabrics to be laminated on the mixed fiber spunbonded nonwoven fabric of the present invention include various known nonwoven fabrics such as spunbonded nonwoven fabrics, melt blown nonwoven fabrics, wet type nonwoven fabrics, dry type nonwoven fabrics, dry type pulp nonwoven fabrics, flash spinning nonwoven fabrics, and split yarn nonwoven fabrics. These nonwoven fabrics may be non-stretching nonwoven fabrics. The non-stretching nonwoven fabrics used herein have an elongation at rupture in MD (direction of the flow of the nonwoven fabric, longitudinal direction) or in CD (the direction perpendicular to the direction of the flow of the nonwoven fabric, transversal direction) of about 50% and do not cause returning stress after elongation.

The films to be laminated on the mixed fiber spunbonded nonwoven fabric of the present invention are preferably breathable (moisture permeable) films capable of making the most of breathability and hydrophilicity which are the properties of the mixed fiber spunbonded nonwoven fabric of the present invention. The breathable films are various known breathable films, for example, moisture permeable films formed from thermoplastic elastomers such as polyurethane elastomer, polyester elastomer, and polyamide elastomer; and porous films obtainable by stretching films formed from inorganic or organic fine particle-containing thermoplastic resins so as to be porous. Preferable examples of thermoplastic resins used in the porous films are polyolefins such as high-pressure low density polyethylene, linear low density polyethylene (namely, LLDPE), high density polyethylene, polypropylene, polypropylene random copolymer and compositions thereof.

<Absorbent Article>

The absorbent articles of the present invention are sanitary napkins, panty liners, incontinence pads, disposable diapers and other products containing the mixed fiber spunbonded nonwoven fabrics. The absorbent articles usually have an intermediate layer made from an absorber provided between a back sheet and a liquid permeable surface sheet.

The mixed fiber spunbonded nonwoven fabric of the present invention has excellent initial hydrophilicity and long-lasting hydrophilicity, and also has excellent liquid dispersibility and liquid transpiration property. Therefore, it can be suitably used for a surface sheet, a second sheet, a sheet (core lap) for lapping absorbing materials, and a back sheet of absorbent articles. Furthermore, the mixed fiber spunbonded nonwoven fabric of the present invention has excellent moisture permeability, breathability, softness, resistance to fluff, stretchability and touch, and low stickiness, and thus it is suitable for the aforementioned uses.

EXAMPLE

Hereinafter, the present invention is described in more detail with reference to the following examples, but the present invention is not limited by the examples.

The physical property values in Examples and Comparative Examples were determined by the following methods. The measurements of (7) liquid dispersion area and (8) liquid evaporation time, described later, employed an aqueous solution of sodium chloride having a surface tension of 70+/−2 mN/m (9 g/liter) as artificial urine.

(1) Basis Weight [g/m$^2$]

Six specimens each having a size of 200 mm (MD)×50 mm (CD) were prepared from a mixed fiber spunbonded nonwoven fabric. They were prepared from any three parts of the fabric in MD and CD (total six places). Then, a mass (g) of each specimen was measured using an electronic even balance (manufactured by Kensei Co., Ltd.). An average value of the masses of the individual specimens was determined, and was converted to a mass (g) per 1 m$^2$, and then, the converted value was rounded to one decimal place, thereby providing a basis weight [g/m$^2$] of each nonwoven fabric sample.

(2) Thickness [μm]

Three specimens each having a size of 100 mm (MD)× 100 mm (CD) were prepared from a mixed fiber spunbonded nonwoven fabric. They were prepared from any three parts of the fabric. Then, a thickness [μm] of each specimen was measured using a load type thickness indicator by the method as described in JIS L 1096. An average value of the thicknesses of the individual specimens was determined, and rounded to one decimal place, thereby providing a thickness [μm] of each nonwoven fabric sample.

(3) Pressed Area Ratio [%]

Five specimens each having a size of 20 mm (MD)×20 mm (CD) were prepared from a partially press treated mixed fiber spunbonded nonwoven fabric. They were prepared from any five parts of the fabric. Then, a press treated area [m$^2$] in each specimen prepared was measured using a ruler, and the measured area was divided by the area of the specimen (400 mm$^2$), thereby calculating a pressed area ratio [%]. An average value of the pressed area ratios of the individual specimens was determined, and rounded to a whole number, thereby providing a pressed area ratio [%] of each nonwoven fabric sample.

(4) Bulk Density [g/cm$^3$]

Using the measurement results of (1) the basis weight and (2) the thickness, conversion based on algebraic calculation was carried out to provide a mass (g) per 1 cm$^3$. The resultant mass was rounded to three decimal places, thereby providing a bulk density [g/cm$^3$] of each nonwoven fabric sample. With regard to the partially press treated mixed fiber nonwoven fabric, from the measurement results of (1) the basis weight, (2) the thickness of the pressed portion, and the thickness of the non-pressed portion, conversion based on algebraic calculation was carried out about the pressed portion and the non-pressed portion to provide a mass (g) per 1 cm$^3$, thereby obtaining a bulk density of the pressed portion and a bulk density of the non-pressed portion. Then, a value obtainable from the following relation using (3) the pressed area ratio was rounded to three decimal places, thereby providing a bulk density [g/cm$^3$] of the partially press treated mixed fiber nonwoven fabric.

Bulk density of a partially pressed mixed fiber spunbonded nonwoven fabric[g/cm$^3$]=Density of a pressed portion×Pressed area ratio+Density of a non-pressed portion×(1−Pressed area ratio)

(5) Fiber Diameter [μm]

A specimen having a size of 100 mm (MD)×50 mm (CD) was prepared from a mixed fiber spunbonded nonwoven fabric. The specimen was photographed in a magnification of 200 times, and the picture was analyzed with a software for measuring image size (Pixs2000 Version 2.0 manufactured by Inotex Co.). With regard to each specimen, the diameters of 10 fibers were measured, and then an average value of the fiber diameters of each specimen was determined, and rounded to one decimal place, thereby providing a fiber diameter [μm] of each nonwoven fabric sample.

(6) Breathability [cm$^3$/cm$^2$/sec]

Five specimens each having a size of 150 mm (MD)×150 mm (CD) were prepared from a mixed fiber spunbonded nonwoven fabric. They were prepared from any five parts of the fabric. Then, each specimen prepared was subjected to measurement using a breathability tester (manufactured by Textest, FX3300) by method A (Frazir method) described in JIS L 1096, thereby measuring breathability [cm$^3$/cm$^2$/sec]. An average value of the breathabilities of the individual specimens was determined, and rounded to a whole number, thereby providing a breathability [cm$^3$/cm$^2$/sec] of each nonwoven fabric sample.

(7) MIU (Average Coefficient of Static Friction) [−]

Three specimens each having a size of 100 mm (MD)× 100 mm (CD) were prepared from a mixed fiber spunbonded nonwoven fabric. They were prepared from any three parts of the fabric. Each specimen prepared was subjected to measurement using a surface friction coefficient friction property tester (KES-SE manufactured by Kato Tech, Co., Ltd.) in accordance with the method described in "Fuai no Hyoka no Hyojyunka to Kaiseki (The standardization and analysis of hand evaluation)" issued by The Textile Machinery Society of Japan. Average values of MIU values in MD and MIU values in CD of the individual specimens were determined, and rounded to two decimal places, thereby providing MIU [-] in MD and CD of each nonwoven fabric sample.

(8) Strength Ratio [%]

Three MD specimens each having a size of 200 mm (MD)×50 mm (CD), and three CD specimens each having a size of 50 mm (MD)×200 mm (CD) were prepared from a mixed fiber spunbonded nonwoven fabric. The MD specimens and the CD specimens were prepared from any three parts of the fabric (total six places). Then, each specimen was subjected to measurement using a universal tensile tester (IM-201 manufactured by INTESCO, Co., Ltd.) under conditions of a distance between chucks of 100 mm and a tensile rate of 100 mm/min, thereby measuring a maximum strength (N) and an elongation at a maximum point (an elongation at the maximum strength) [%]. By multiplying the elongation at a maximum point by 0.2, an elongation X [%] was calculated, and a strength X at the elongation X [N] was determined, and was divided by the maximum strength, thereby obtaining a strength ratio. Average values each for the three MD specimens and CD specimens were determined and rounded to a whole number, thereby providing MD and CD strength ratios [%] of each nonwoven fabric sample.

(9) Liquid Dispersion Area [cm$^2$]

Three specimens each having a size of 200 mm (MD)× 200 mm (CD) were prepared from a mixed fiber spunbonded nonwoven fabric. They were prepared from any three parts of the fabric. Each specimen prepared was placed on a flat acrylic plate. Under environment of 23° C.×50% RH, 1 mL of the artificial urine was dropped with a dropper on the surface of the specimen from the height of about 10 mm from the surface of the specimen. After the permeation of the artificial urine, the dispersion state of the artificial urine widespread across the surface of the sample was measured in MD and CD.

Then, the dispersion distance in MD was defined as M [cm], and the dispersion distance in CD was defined as C [cm], and the liquid dispersion area of each specimen was measured on the basis of the following relation.

Liquid dispersion area[cm$^2$]=3.14×(M/2)×(C/2)

An average value of the liquid dispersion areas of the individual specimens was determined, and rounded to one decimal place, thereby providing a liquid dispersion area [cm$^2$] of each nonwoven fabric sample. A larger liquid dispersion area was evaluated as a higher liquid dispersibility.

(10) Liquid Evaporation Time [min]

Three specimens each having a size of 200 mm (MD)× 200 mm (CD) were prepared from a mixed fiber spunbonded nonwoven fabric. Each specimen was subjected to measurement using an electronic even balance (manufactured by Kensei Co., Ltd.), thereby measuring each mass (g). They were prepared from any three parts of the fabric. Then, each specimen prepared was placed on a flat acrylic plate. Under environment of 23° C.×50% RH, 1 mL of the artificial urine was dropped with a dropper on the surface of the specimen from the height of about 10 mm from the surface of the specimen. Every five minutes, a mass (g) was measured by the method as described above, and time taken for the mass to become the mass measured before the dropping was defined as liquid evaporation time [min]. An average value of the liquid evaporation times for the individual specimens was determined, and rounded to a whole number, thereby providing a liquid evaporation time [min] of each nonwoven fabric sample. When the mass did not become the mass measured before the dropping even after the passage of 180 minutes from the dropping, the liquid evaporation time was evaluated as being not less than 180 minutes.

(11) Touch

Ten panelists checked the touch of a mixed fabric spunbonded nonwoven fabric and evaluated in accordance with the following criteria.

H: Among 10 panelists, 10 panelists judged that the specimen had no stickiness and felt good touch.

I: Among 10 panelists, 9 to 7 panelists judged that the specimen had no stickiness and felt good touch.

J: Among 10 panelists, 6 to 3 panelists judged that the specimen had no stickiness and felt good touch.

K: Among 10 panelists, 2 to 0 panelists judged that the specimen had no stickiness and felt good touch.

The analysis and evaluation on the thermoplastic polyurethane elastomer (TPU) used in the examples and the comparative examples were carried out in the following methods.

(12) Solidification Starting Temperature [° C.]

The measurement was carried out using a differential scanning calorimeter (DSC220C) connected with SSC5200 H disk station manufactured by Seiko Instruments Inc. As a sample, about 8 mg of TPU pulverized was collected on an aluminum pan and crimped with a cover. As a reference, alumina was collected in the same manner. The sample and the reference were set in the prescribed positions in a cell and measured in a stream of nitrogen at a flow rate of 40 Nml/min. The temperature was increased from room temperature to 230° C. at an increasing rate of 10° C./min and kept at the same temperature for 5 min and then decreased to −75° C. at a decreasing rate of 10° C./min. At this time, the starting temperature of an exothermic peak derived from solidification of TPU was measured and taken as a solidification starting temperature (unit: ° C.).

(13) Number of Particles Insoluble in DMAC Solvent [Particles/g]

The measurement was carried out using Multisizer II manufactured by Beckman Coulter K.K., as a particle size distribution measuring apparatus based on an electrical sensing zone method. In a 5 L separable flask, 3500 g of dimethylacetoamide (DMAC, special grade, manufactured by Wako Pure Chemical Industries) and 145.83 g of thiocyanic acid ammonium (special grade manufactured by Junsei Chemical Co., Ltd.) were weighed and dissolved at room temperature over 24 hr.

Subsequently, filtration was carried out under reduced pressure using a 1 μm membrane filter and thereby a reagent A was prepared. In a 200 cc glass bottle, 180 g of the reagent A and 2.37 g of a TPU pellet were weighed and the soluble part in TPU was dissolved over 3 hr to prepare a measuring specimen. To Multisizer II, a 100 μm aperture tube was fixed and the solvent in the device was replaced with the reagent A, and then the vacuum pressure was regulated to about 3000 mmAq. In a beaker for introducing the specimen which beaker had been thoroughly cleaned, 120 g of the reagent A was weighed and it was confirmed that the amount of the pulse generated by the blank measurement was not more than 50 pulses/min. The optimum current value and gain were set in accordance with the manual and then calibration was carried out using uncrosslinked polystyrene standard particles having a size of 10 μm. The measurement was carried out for 210 sec after 120 g of the reagent A and about 10 g of the measurement specimen were weighed in a specimen-introducing beaker thoroughly washed. The particle number counted in the measurement was divided by the TPU weight sucked in the aperture tube to determine the number of the particles insoluble in the DMAC solvent in TPU (unit: particles/g). The weight of TPU was determined by the following formula.

TPU weight={[(A)/100)×(B)/[(B)+(C)]]×(D)

In the formula, (A) is a concentration (% by weight) of TPU of the specimen for measurement, (B) is a weight (g) of the specimen for measurement weighed in the beaker, (C) is a weight (g) of the reagent A weighed in the beaker, and (D) is a weight (g) of a solution sucked in the aperture tube during the measurement (210 sec).

(14) Ratio of Heat of Fusion in Hard Domain

The heat of fusion was measured by a differential scanning calorimeter (DSC220C) connected to SSC5200H disk station manufactured by Seiko Electronic Industries. As a sample, about 8 mg of TPU pulverized was collected in an aluminum pan and crimped by a cover. As a reference, alumina was collected in the same manner. The sample and the reference were set in the prescribed positions in a cell and measured in a stream of nitrogen at a flow rate of 40 Nml/min. The temperature was increased from room temperature to 230° C. at an increasing rate of 10° C./min. The total sum (a) of heat of fusion determined from an endothermic peak at a peak temperature of not lower than 90° C. and not higher than 140° C. and the total sum (b) of heat of fusion determined from an endothermic peak at a peak temperature of higher than 140° C. and not higher than 220° C. were determined and the ratio of heat of fusion of the hard domain (unit: %) was determined by the following formula.

Ratio of heat of fusion in hard domain (%)=a/(a+b)×100

(15) Melt Viscosity at 200° C. (Hereinafter Referred to "Melt Viscosity" Simply)

Using Capiro Graph (model 1C manufactured by Toyo Seiki Co., Ltd.), the melt viscosity (unit: Pa·s) at 200° C. at a shear rate of 100 sec$^1$ was measured. A nozzle having a length of 30 mm and a diameter of 1 mm was used.

(16) Water Content of TPU

The water content of TPU (unit: ppm) was measured in combination use of a water content measuring device (AVQ-5S manufactured by Hiranuma Sangyo Co., Ltd.) and a water content vaporizer (EV-6 manufactured by Hiranuma Sangyo Co., Ltd.). About 2 g of TPU pellets was weighed in a heating specimen pan and introduced into a heating furnace at 250° C. Vaporized moisture was led to a titration cell of the water content measuring device which residual moisture had been removed previously and titration was carried out by a Karl Fisher reagent. It was confirmed that the potential change of a titration electrode accompanied with the water content change in the cell was not caused for 20 sec to finish the titration.

(17) Shore A Hardness

The hardness of TPU was measured at 23° C. at a relative humidity of 50% in accordance with the method as described in JIS K-7311. The type A was used as a durometer.

<Preparation Example 1 of Thermoplastic Polyurethane Elastomer>

Diphenylmethane diisocyanate (hereinafter referred to as MDI) was introduced into a tank in a nitrogen atmosphere and regulated with stirring in such a way that bubbles were not mixed to be at 45° C.

To a tank B, 628.6 parts by weight of polyester polyol having a number average molecular weight of 2000 (product name: Takelack U2024 manufactured by Mitsui Takeda Chemicals Inc.) and 2.21 parts by weight of Irganox 1010 and 77.5 parts by weight of 1,4-butane diol were introduced in a nitrogen atmosphere and regulated with stirring to be at 95° C. This mixture was provided as a polyol solution 1.

The hard segment amount calculated from these reaction raw materials was 37.1% by weight.

Next, in a liquid transporting line with a gear pump and a flowmeter, MDI was passed through at a rate of 17.6 Kg/h and the polyol solution 1 was passed through at a rate of 42.4 Kg/h to a high speed stirrer (SM40) regulated at 120° C. quantitatively and mixed with stirring at 2000 rpm for 2 min. Thereafter the mixture was passed through to a static mixer. The static mixer part was composed of the following mixtures connected in series: first to third static mixers (temperature 230° C.) prepared by connecting three static mixers having a tube length of 0.5 m and an inner diameter of 20 mmϕ, fourth to sixth static mixers (temperature 220° C.) prepared by connecting three static mixers having a tube length of 0.5 m and an inner diameter of 20 mmϕ, seventh to twelfth static mixers (temperature 210° C.) prepared by connecting six static mixers having a tube length of 1.0 m and an inner diameter of 34 mmϕ, and thirteenth to fifteenth static mixers (temperature 200° C.) prepared by connecting three static mixers having a tube length of 0.5 m and an inner diameter of 38 mmϕ.

The reaction product drained from the fifteenth static mixer was fed with pressure to a mono-axial extruder (diameter: 65 mmϕ, temperature: 180 to 210° C.) with a polymer filter (product name, Dina filter manufactured by Nagase Co., Ltd.) on the tip through the gear pump and extruded from a strand die. After cooling with water, the extruded product was continuously pelletized. Subsequently, the resulting pellets were introduced into a dryer and dried at 100° C. for 8 hr to prepare a thermoplastic polyurethane elastomer having a water content of 40 ppm. This thermoplastic polyurethane elastomer was continuously extruded by a mono-axial extruder (diameter: 50 mmϕ, temperature: 180 to 210° C.) to be pelletized. The pellets were dried again at 100° C. for 7 hr to prepare a thermoplastic polyurethane elastomer (B-1) having a water content of 57 ppm.

The starting temperature of solidifying B-1 was 103.7° C., the number of the particles insoluble in the DMAC solvent was 1,500,000 particles/g, the specimen prepared by injection molding had a hardness of 86A and a melt viscosity at 200° C. of 1900 Pa·s and ratio of heat of fusion of the hard domain was 35.2%.

Example 1

<Preparation of Thermoplastic Resin Composition for Mixed Fiber Spunbonded Nonwoven Fabric>

Into 60% by weight of an ethylene oxide adduct of eicosanol [$CH_3(CH_2)_{19}$—O—$(CH_2CH_2O)_{2.5}$—H] and 40% by weight of a propylene homopolymer having a MFR of 30 g/10 min, 0.05 part by weight of antioxidant (manufactured by Ciba, product name: Irgafos 168) was added. The mixture was melt-kneaded at 230° C., and extruded, thereby preparing a pelletized masterbatch (hydrophilizing agent AE-1).

96% by weight of a propylene homopolymer having a MFR, as determined in accordance with ASTM D 1238, at 230° C. under a load of 2.16 Kg, of 60 g/10 min, a density of 0.91 g/cm$^3$, a melting point of 160° C. (hereinafter referred to as "PP-1") was mixed with 4% by weight of a high density polyethylene having a MFR, as determined in accordance with ASTM D 1238, at 190° C. under a load of 2.16 Kg, of 5 g/10 min, a density of 0.97 g/cm³, a melting point of 134° C. (hereinafter referred to "HDPE"). Thereafter, with 100 parts by weight of the PP-1/HDPE composition, 5 parts by weight (3 parts by weight in terms of a hydrophilization treatment agent component) of the hydrophilizing agent (AE-1) was mixed to prepare a thermoplastic resin composition (A-1).

<Production of Mixed Fiber Spunbonded Nonwoven Fabric Layer>

The thermoplastic polyurethane elastomer (B-1) and the thermoplastic resin composition (A-1) were independently melted using a 75 mmφ extruder and a 50 mmφ extruder. Thereafter, using a spunbonding nonwoven molding machine having a spinning die (length vertical to the machine direction on the collecting surface: 800 mm), they were melt spun at a resin temperature of 210° C., at a die temperature of 210° C., at a cooling air temperature of 20° C., at a stretching air rate of 3750 m/min, by a spunbonding method, and a web made from mixed long fibers containing a long fiber b-1 of B-1 and a long fiber a-1 of A-1 was deposited on the collecting surface to prepare a web of mixed fibers of the long fiber b-1 and the long fiber a-1 in the proportion of 50/50 (% by weight). The spinning die had a nozzle pattern such that an output hole for b-1 and an output hole for a-1 were alternately disposed. The nozzle diameter for b-1 (fiber b-1) was 0.75 mmφ and the nozzle diameter for A-1 (long fiber a-1) was 0.6 mmφ, the nozzle pitch was 8 mm in the longitudinal direction and 11 mm in the transversal direction, and the nozzle number ratio of the nozzle for the fiber b-1 to the nozzle for the long fiber a-1 was 1/1.45. The output amount of the single hole for the long fiber b-1 was 1.08 g/(min·hole) and the output amount of the single hole for the long fiber a-1 was 0.74 g/(min·hole).

The web made from the mixed long fiber deposited was nipped with a nip roll coated with a non-adhesive material disposed on a belt (linear pressure: 10 N/cm) and then pealed from the moving belt, thereby obtaining a mixed fiber spunbonded web layer 1. The mixed fiber spunbonded web layer 1 obtained had a basis weight of 30 g/m².

By the same method as described above, a mixed fiber spunbonded web layer 2 (basis weight: 30 g/m²) was obtained.

Then, the mixed fiber spunbonded web layer 1 and the mixed fiber spunbonded web layer 2 were superposed with each other, and they were heat bonded by heat embossing under the conditions such that they had an emboss pattern of an area ratio of 18% and an embossed area of 0.41 mm², and the heating temperature was 105° C. and the linear pressure was 70 N/cm, to obtain a laminated mixed fiber spunbonded web layer (1/2).

The mixed fiber spunbonded web layer (1/2) obtained was gear-stretched in CD (transversal direction) using a gear processing machine as shown in FIGS. 1 and 2. With regard to gear rolls mounted on the gear processing machine, the diameter of each roll was 200 mm, and the gear pitch was 2.5 mm, and the depth of the meshing of both the rolls was adjusted to be 4.5 mm. The stretching ratio obtained by this method was 374% (a ratio of 3.74).

Then, by carrying out press processing using a heated roll having a heating temperature of 120° C. and a linear pressure of 30 N/cm, a mixed fiber spunbonded nonwoven fabric was obtained. The mixed fiber spunbonded nonwoven fabric obtained had a basis weight of 62 g/m². The mixed fiber spunbonded nonwoven fabric obtained was evaluated by the method as described above. The evaluation result is shown in Table 1. The touch (11) was evaluated as "I". When this mixed fiber spunbonded nonwoven fabric was stretched in CD, good stretchability was obtained.

Example 2

A mixed fiber spunbonded nonwoven fabric was prepared by the same manner as in Example 1, except that the conditions of the press processing performed in Example 1 were changed such that the heating temperature was 105° C. and the linear pressure was 30 N/cm, and the mixed fiber spunbonded nonwoven fabric was evaluated by the method as described above. The evaluation result is shown in Table 1. The touch (11) was evaluated as "I". When this mixed fiber spunbonded nonwoven fabric was stretched in CD, good stretchability was obtained.

Example 3

A mixed fiber spunbonded nonwoven fabric was prepared by the same manner as in Example 2, except that in the stretch processing performed in Example 2, the depth of the meshing of the rolls was adjusted to be 2.5 mm. The stretching ratio in CD obtained under the above conditions was 220% (a ratio of 2.2). This mixed fiber spunbonded nonwoven fabric was evaluated by the method as described above. The evaluation result is shown in Table 1. The touch (11) was evaluated as "I". When this mixed fiber spunbonded nonwoven fabric was stretched in CD, good stretchability was obtained.

Comparative Example 1

The mixed fiber spunbonded web layer (1/2) obtained in Example 1 was not subjected to stretch processing and press processing, and was evaluated by the method as described above. The evaluation result is shown in Table 1.

Comparative Example 2

The mixed fiber spunbonded web layer (1/2) obtained in Example 1 was subjected to stretch processing described in Example 1 alone, and was evaluated by the method as described above. The evaluation result is shown in Table 1.

Comparative Example 3

The mixed fiber spunbonded web layer (1/2) obtained in Example 1 was subjected to press processing described in Example 1 alone, and was evaluated by the method as described above. The evaluation result is shown in Table 1.

TABLE 1

| Example/Comparative Example | | Example 1 | | Example 2 | | Example 3 | |
|---|---|---|---|---|---|---|---|
| First Layer | Fiber form | Mixed fiber | | Mixed fiber | | Mixed fiber | |
| | | b-1 | a-1 | b-1 | a-1 | b-1 | a-1 |
| | Weight proportion (%) | 50 | 50 | 50 | 50 | 50 | 50 |
| | Polymer | B-1 | PP-1 | B-1 | PP-1 | B-1 | PP-1 |
| | (part by weight) | (100) | (96) | (100) | (96) | (100) | (96) |
| | | — | HDPE (4) | — | HDPE (4) | — | HDPE (4) |
| | Hydrophilizing agent (part by weight) | — | AE-1 (5) | — | AE-1 (5) | — | AE-1 (5) |
| | Starting temperature for solidification of TPU | 103.7° C. | | 103.7° C. | | 103.7° C. | |
| | Particle number of components insoluble in DMAC solvent in TPU | $150 \times 10^4$ particles/g | | $150 \times 10^4$ particles/g | | $150 \times 10^4$ particles/g | |
| | TPU shore A hardness | 86 | | 86 | | 86 | |
| | Molding method | Spunbond | | Spunbond | | Spunbond | |
| | Fusion method | No | | No | | No | |
| | Stretching treatment | No | | No | | No | |
| | Pressing treatment (area ratio) | No | | No | | No | |
| | Basis weight (g/m²) | 30 | | 30 | | 30 | |
| Second Layer | Fiber form | Mixed fiber | | Mixed fiber | | Mixed fiber | |
| | | b-1 | a-1 | b-1 | a-1 | b-1 | a-1 |
| | Weight proportion (%) | 50 | 50 | 50 | 50 | 50 | 50 |
| | Polymer | B-1 | PP-1 | B-1 | PP-1 | B-1 | PP-1 |
| | (part by weight) | (100) | (96) | (100) | (96) | (100) | (96) |
| | | — | HDPE (4) | — | HDPE (4) | — | HDPE (4) |
| | Hydrophilizing agent (part by weight) | — | AE-1 (5) | — | AE-1 (5) | — | AE-1 (5) |
| | Starting temperature for solidification of TPU | 103.7° C. | | 103.7° C. | | 103.7° C. | |
| | Particle number of components insoluble in DMAC solvent in TPU | $150 \times 10^4$ particles/g | | $150 \times 10^4$ particles/g | | $150 \times 10^4$ particles/g | |
| | TPU shore A hardness | 86 | | 86 | | 86 | |
| | Molding method | Spunbond | | Spunbond | | Spunbond | |
| | Fusion method | No | | No | | No | |
| | Stretching treatment | No | | No | | No | |
| | Pressing treatment (area ratio) | No | | No | | No | |
| | Basis weight (g/m²) | 30 | | 30 | | 30 | |

| Example/Comparative Example | | Comparative Example 1 | | Comparative Example 2 | | Comparative Example 3 | |
|---|---|---|---|---|---|---|---|
| First Layer | Fiber form | Mixed fiber | | Mixed fiber | | Mixed fiber | |
| | | b-1 | a-1 | b-1 | a-1 | b-1 | a-1 |
| | Weight proportion (%) | 50 | 50 | 50 | 50 | 50 | 50 |
| | Polymer | B-1 | PP-1 | B-1 | PP-1 | B-1 | PP-1 |
| | (part by weight) | (100) | (96) | (100) | (96) | (100) | (96) |
| | | — | HDPE (4) | — | HDPE (4) | — | HDPE (4) |
| | Hydrophilizing agent (part by weight) | — | AE-1 (5) | — | AE-1 (5) | — | AE-1 (5) |
| | Starting temperature for solidification of TPU | 103.7° C. | | 103.7° C. | | 103.7° C. | |
| | Particle number of components insoluble in DMAC solvent in TPU | $150 \times 10^4$ particles/g | | $150 \times 10^4$ particles/g | | $150 \times 10^4$ particles/g | |
| | TPU shore A hardness | 86 | | 86 | | 86 | |
| | Molding method | Spunbond | | Spunbond | | Spunbond | |
| | Fusion method | No | | No | | No | |
| | Stretching treatment | No | | No | | No | |
| | Pressing treatment (area ratio) | No | | No | | No | |
| | Basis weight (g/m²) | 30 | | 30 | | 30 | |

TABLE 1-continued

| Second Layer | Fiber form | Mixed fiber | | Mixed fiber | | Mixed fiber | |
|---|---|---|---|---|---|---|---|
| | | b-1 | a-1 | b-1 | a-1 | b-1 | a-1 |
| | Weight proportion (%) | 50 | 50 | 50 | 50 | 50 | 50 |
| | Polymer (part by weight) | B-1 (100) | PP-1 (96) | B-1 (100) | PP-1 (96) | B-1 (100) | PP-1 (96) |
| | | — | HDPE (4) | — | HDPE (4) | — | HDPE (4) |
| | Hydrophilizing agent (wt %) | — | AE-1 (5) | — | AE-1 (5) | — | AE-1 (5) |
| | Starting temperature for solidification of TPU | 103.7° C. | | 103.7° C. | | 103.7° C. | |
| | Particle number of components insoluble in DMAC solvent in TPU | $150 \times 10^4$ particles/g | | $150 \times 10^4$ particles/g | | $150 \times 10^4$ particles/g | |
| | TPU shore A hardness | 86 | | 86 | | 86 | |
| | Molding method | Spunbond | | Spunbond | | Spunbond | |
| | Fusion method | No | | No | | No | |
| | Stretching treatment | No | | No | | No | |
| | Pressing treatment (area ratio) | No | | No | | No | |
| | Basis weight (g/m²) | 30 | | 30 | | 30 | |

| Example/Comparative Example | | Example 1 | Example 2 | Example 3 | Comparative Example 1 | Comparative Example 2 | Comparative Example 3 |
|---|---|---|---|---|---|---|---|
| Lamination method of each layer | | Heat embossing | Heat embossing | Heat embossing | Heat embossing | Heat embossing | Heat embossing |
| Processing method after lamination | Stretching treatment | CD × 374% | CD × 374% | CD × 220% | No | CD × 374% | No |
| | Pressing treatment (area ratio) | 120° C. × 30 N/cm (100%) | 105° C. × 30 N/cm (100%) | 105° C. × 30 N/cm (100%) | No | No | 120° C. × 30 N/cm (100%) |
| Surface measured (surface on which liquid was dropped) | | First layer | First layer | First layer | First layer | First layer | First layer |
| Basis weight (g/m²) | | 62 | 62 | 62 | 62 | 62 | 62 |
| Thickness (mm) | | 0.22 | 0.38 | 0.52 | 0.71 | 1.07 | 0.63 |
| Bulk density (g/cm³) | | 0.28 | 0.16 | 0.12 | 0.09 | 0.06 | 0.10 |
| Fiber diameter (μm) | | 20.2 | 20.6 | 21.3 | 23.2 | 20.2 | 22.6 |
| Breathability (cm³/cm²/sec) | | 52 | 123 | 107 | 180 | 428 | 87 |
| MIU (−) | MD | 1.98 | 2.04 | 2.22 | 2.34 | 2.65 | 2.20 |
| | CD | 2.26 | 2.40 | 2.34 | 2.68 | 2.97 | 2.35 |
| Strength ratio (%) | MD | 59 | 73 | 86 | 53 | 41 | 41 |
| | CD | 18 | 15 | 30 | 57 | 10 | 53 |
| Liquid dispersion area (cm²) | | 125 | 76 | 70 | 40 | 10 | 43 |
| Liquid evaporation time (min) | | 20 | 55 | 60 | not less than 180 | not less than 180 | not less than 180 |

Example 4

<Preparation of Thermoplastic Resin Composition for Mixed Fiber Spunbonded Nonwoven Fabric>

96% by weight of PP-1 was mixed with 4% by weight of HDPE, and then, with 100 parts by weight of the PP-1/HDPE mixture, 10.7 parts by weight (6.42 parts by weight in terms of a hydrophilization treatment agent component) of the hydrophilizing agent (AE-1) was mixed to prepare a thermoplastic resin composition (A-2).

Subsequently, 96% by weight of PP-1 was mixed with 4% by weight of HDPE, and then, with 100 parts by weight of the PP-1/HDPE mixture, 1.8 parts by weight (0.65 part by weight in terms of a hydrophilization treatment agent component) of the hydrophilizing agent (AE-1) was mixed to prepare a thermoplastic resin composition (A-3).

<Production of Mixed Fiber Spunbonded Nonwoven Fabric Layer>

The thermoplastic polyurethane elastomer (B-1) and the thermoplastic resin composition (A-2) were independently melted using a 75 mmϕ extruder and a 50 mmϕ extruder. Thereafter, using a spunbonding nonwoven molding machine having a spinning die (length vertical to the machine direction on the collecting surface: 800 mm), they were melt spun at a resin temperature of 210° C., at a die temperature of 210° C., at a cooling air temperature of 20° C., at a stretching air rate of 3750 m/min, by a spunbonding method, and a web made from mixed long fibers containing a long fiber b-1 of B-1 and a long fiber a-2 of A-2 was deposited on the collecting surface to prepare a web of mixed fibers of the long fiber b-1 and the long fiber a-2 in the proportion of 65/35 (% by weight). The spinning die had a nozzle pattern such that an output hole for B-1 and an output hole for A-2 were alternately disposed. The nozzle diameter for B-1 (long fiber b-1) was 0.75 mmϕ and the nozzle diameter for A-2 (long fiber a-2) was 0.6 mmϕ, the nozzle pitch was 8 mm in the longitudinal direction and 11 mm in the transversal direction and the nozzle number ratio of the nozzle for the long fiber b-1 to the nozzle for the long fiber a-2 was 1/1.45. The output amount of the single hole for the long fiber b-1 was 1.40 g/(min·hole) and the output amount of the single hole for the long fiber a-2 was 0.52 g/(min·hole).

The web made from the mixed long fiber deposited was nipped with a nip roll coated with a non-adhesive material disposed on a belt (linear pressure: 10 N/cm) and then pealed from the moving belt, thereby obtaining a mixed fiber spunbonded web layer 3. The mixed fiber spunbonded web layer 3 obtained had a basis weight of 30 g/m².

Subsequently, the thermoplastic polyurethane elastomer (B-1) and the thermoplastic resin composition (A-3) were independently melted using a 75 mmφ extruder and a 50 mmφ extruder. Thereafter, using a spunbonding nonwoven molding machine having a spinning die (length vertical to the machine direction in the collecting surface: 800 mm), they were melt spun at a resin temperature of 210° C., at a die temperature of 210° C., at a cooling air temperature of 20° C., at a stretching air rate of 3750 m/min, by a spunbonding method, and a web made from mixed long fibers containing a long fiber b-1 of B-1 and a long fiber a-3 of A-3 was deposited on the collecting surface to prepare a web of mixed fibers of the long fiber b-1 and the long fiber a-3 in the proportion of 30/70 (% by weight). The spinning die had a nozzle pattern such that an output hole for B-1 and an output hole for A-3 were alternately disposed. The nozzle diameter for B-1 (long fiber b-1) was 0.75 mmφ and the nozzle diameter for A-3 (long fiber a-3) was 0.6 mmφ, the nozzle pitch was 8 mm in the longitudinal direction and 11 mm in the transversal direction and the nozzle number ratio of the nozzle for the long fiber b-1 to the nozzle for the long fiber a-3 was 1/1.45. The output amount of the single hole for the long fiber b-1 was 1.65 g/(min·hole) and the output amount of the single hole for the long fiber a-3 was 1.04 g/(min·hole).

The web made from the mixed long fiber deposited was nipped with a nip roll coated with a non-adhesive material disposed on a belt (linear pressure: 10 N/cm) and then pealed from the moving belt, thereby obtaining a mixed fiber spunbonded web layer 4. The mixed fiber spunbonded web layer 4 obtained had a basis weight of 30 g/m².

<Production of Mixed Fiber Spunbonded Nonwoven Fabric>

The mixed fiber spunbonded web layer 3 and the mixed fiber spunbonded web layer 4 were superposed with each other, and they were heat bonded by heat embossing under the conditions such that they had an emboss pattern of an area ratio of 18% and an embossed area of 0.41 mm², and the heating temperature was 105° C. and the linear pressure was 70 N/cm, to obtain a laminated mixed fiber spunbonded web layer (3/4).

The mixed fiber spunbonded web layer (3/4) obtained was subjected to stretch processing and press processing in the same method as in Example 3, thereby obtaining a mixed fiber spunbonded nonwoven fabric. The mixed fiber spunbonded web layer 3 of the mixed fiber spunbonded nonwoven fabric obtained was defined as a surface, and the surface was evaluated in the same manner as described above. The evaluation result is shown in Table 2. The touch (11) was evaluated as "I". When this mixed fiber spunbonded nonwoven fabric was stretched in CD, good stretchability was obtained.

Example 5

The mixed fiber spunbonded web layer (3/4) obtained was subjected to stretch processing and press processing in the same method as in Example 3, thereby obtaining a mixed fiber spunbonded nonwoven fabric. The mixed fiber spunbonded web layer 4 of the mixed fiber spunbonded nonwoven fabric obtained was defined as a surface, and the surface was evaluated in the same manner as described above. The evaluation result is shown in Table 2. The touch (11) was evaluated as "I". When this mixed fiber spunbonded nonwoven fabric was stretched in CD, good stretchability was obtained.

Example 6

The mixed fiber spunbonded web layer (3/4) obtained was subjected to stretch processing in the same method as in Example 1, and then to press processing in the same method as in Example 2, thereby obtaining a mixed fiber spunbonded nonwoven fabric. The mixed fiber spunbonded web layer 3 of the mixed fiber spunbonded nonwoven fabric obtained was defined as a surface, and the surface was evaluated in the same manner as described above. The evaluation result is shown in Table 2. The touch (11) was evaluated as "I". When this mixed fiber spunbonded nonwoven fabric was stretched in CD, good stretchability was obtained.

Example 7

The mixed fiber spunbonded web layer (3/4) obtained was subjected to stretch processing in the same method as in Example 1, and then to press processing in the same method as in Example 2, thereby obtaining a mixed fiber spunbonded nonwoven fabric. The mixed fiber spunbonded web layer 4 of the mixed fiber spunbonded nonwoven fabric obtained was defined as a surface, and the surface was evaluated in the same manner as described above. The evaluation result is shown in Table 2. The touch (11) was evaluated as "I". When this mixed fiber spunbonded nonwoven fabric was stretched in CD, good stretchability was obtained.

Example 8

A mixed fiber spunbonded web layer having 60 g/cm² was obtained in the same method as in Example 1, and then was subjected to stretch processing and press processing in the same method as in Example 1, thereby obtaining a mixed fiber spunbonded nonwoven fabric. The mixed fiber spunbonded nonwoven fabric obtained had a basis weight of 61 g/m². The mixed fiber spunbonded nonwoven fabric obtained was evaluated by the method as described above. The evaluation result is shown in Table 2. The touch (11) was evaluated as "I". When this mixed fiber spunbonded nonwoven fabric was stretched in CD, good stretchability was obtained.

TABLE 2

| Example/Comparative Example | | Example 4 | | Example 5 | | Example 6 | |
|---|---|---|---|---|---|---|---|
| First Layer | Fiber form | Mixed fiber | | Mixed fiber | | Mixed fiber | |
| | | b-1 | a-2 | b-1 | a-2 | b-1 | a-2 |
| | Weight proportion (%) | 65 | 35 | 65 | 35 | 65 | 35 |
| | Polymer (part by weight) | B-1 (100) | PP-1 (96) | B-1 (100) | PP-1 (96) | B-1 (100) | PP-1 (96) |
| | | — | HDPE (4) | — | HDPE (4) | — | HDPE (4) |
| | Hydrophilizing agent (part by weight) | — | AE-1 (10.7) | — | AE-1 (10.7) | — | AE-1 (10.7) |
| | Starting temperature for solidification of TPU | 103.7° C. | | 103.7° C. | | 103.7° C. | |
| | Particle number of components insoluble in DMAC solvent in TPU | $150 \times 10^4$ particles/g | | $150 \times 10^4$ particles/g | | $150 \times 10^4$ particles/g | |
| | TPU shore A hardness | 86 | | 86 | | 86 | |
| | Molding method | Spunbond | | Spunbond | | Spunbond | |
| | Fusion method | No | | No | | No | |
| | Stretching treatment | No | | No | | No | |
| | Pressing treatment (area ratio) | No | | No | | No | |
| | Basis weight (g/m$^2$) | 30 | | 30 | | 30 | |
| Second Layer | Fiber form | Mixed fiber | | Mixed fiber | | Mixed fiber | |
| | | b-1 | a-3 | b-1 | a-3 | b-1 | a-3 |
| | Weight proportion (%) | 30 | 70 | 30 | 70 | 30 | 70 |
| | Polymer (part by weight) | B-1 (100) | PP-1 (96) | B-1 (100) | PP-1 (96) | B-1 (100) | PP-1 (96) |
| | | — | HDPE (4) | — | HDPE (4) | — | HDPE (4) |
| | Hydrophilizing agent (part by weight) | — | AE-1 (1.8) | — | AE-1 (1.8) | — | AE-1 (1.8) |
| | Starting temperature for solidification of TPU | 103.7° C. | | 103.7° C. | | 103.7° C. | |
| | Particle number of components insoluble in DMAC solvent in TPU | $150 \times 10^4$ particles/g | | $150 \times 10^4$ particles/g | | $150 \times 10^4$ particles/g | |
| | TPU shore A hardness | 86 | | 86 | | 86 | |
| | Molding method | Spunbond | | Spunbond | | Spunbond | |
| | Fusion method | No | | No | | No | |
| | Stretching treatment | No | | No | | No | |
| | Pressing treatment (area ratio) | No | | No | | No | |
| | Basis weight (g/m$^2$) | 30 | | 30 | | 30 | |

| Example/Comparative Example | | Example 7 | | Example 8 | |
|---|---|---|---|---|---|
| First Layer | Fiber form | Mixed fiber | | Mixed fiber | |
| | | b-1 | a-2 | b-1 | a-1 |
| | Weight proportion (%) | 65 | 35 | 50 | 50 |
| | Polymer (part by weight) | B-1 (100) | PP-1 (96) | B-1 (100) | PP-1 (96) |
| | | — | HDPE (4) | — | HDPE (4) |
| | Hydrophilizing agent (part by weight) | — | AE-1 (10.7) | — | AE-1 (5) |
| | Starting temperature for solidification of TPU | 103.7° C. | | 103.7° C. | |
| | Particle number of components insoluble in DMAC solvent in TPU | $150 \times 10^4$ particles/g | | $150 \times 10^4$ particles/g | |
| | TPU shore A hardness | 86 | | 86 | |
| | Molding method | Spunbond | | Spunbond | |
| | Fusion method | No | | Heat embossing | |
| | Stretching treatment | No | | CD × 374% | |
| | Pressing treatment (area ratio) | No | | 120° C. × 30 N/cm (100%) | |
| | Basis weight (g/m$^2$) | 30 | | 60 | |

TABLE 2-continued

| Second Layer | Fiber form | Mixed fiber | | — | — |
|---|---|---|---|---|---|
| | | b-1 | a-3 | | |
| | Weight proportion (%) | 30 | 70 | — | — |
| | Polymer | B-1 | PP-1 | — | — |
| | (part by weight) | (100) | (96) | — | — |
| | | — | HDPE | — | — |
| | | | (4) | | |
| | Hydrophilizing agent | — | AE-1 | — | — |
| | (part by weight) | | (1.8) | | |
| | Starting temperature for solidification of TPU | 103.7° C. | | — | — |
| | Particle number of components insoluble in DMAC solvent in TPU | 150 × 10⁴ particles/g | | — | — |
| | TPU shore A hardness | 86 | | — | — |
| | Molding method | Spunbond | | — | — |
| | Fusion method | No | | — | — |
| | Stretching treatment | No | | — | — |
| | Pressing treatment (area ratio) | No | | — | — |
| | Basis weight (g/m²) | 30 | | — | — |

| Example/Comparative Example | | Example 4 | Example 5 | Example 6 | Example 7 | Example 8 |
|---|---|---|---|---|---|---|
| Lamination method of each layer | | Heat embossing | Heat embossing | Heat embossing | Heat embossing | — |
| Processing method after lamination | Stretch treatment | CD × 220% | CD × 220% | CD × 374% | CD × 374% | — |
| | Pressing treatment (area ratio) | 105° C. × 30 N/cm (100%) | 105° C. × 30 N/cm (100%) | 105° C. × 30 N/cm (100%) | 105° C. × 30 N/cm (100%) | — |
| Surface measured (surface on which liquid was dropped) | | First layer | Second layer | First layer | Second layer | First layer |
| Basis weight (g/m²) | | 55 | 55 | 55 | 55 | 61 |
| Thickness (mm) | | 0.31 | 0.31 | 0.3 | 0.3 | 0.22 |
| Bulk density (g/cm³) | | 0.17 | 0.17 | 0.18 | 0.18 | 0.28 |
| Fiber diameter (pm) | | 20.2 | 20.5 | 21.8 | 21.8 | 20.4 |
| Breathability (cm³/cm²/sec) | | 112 | 112 | 96 | 96 | 52 |
| MIU (—) | MD | 2.12 | 2.04 | 2.09 | 1.91 | 1.92 |
| | CD | 2.64 | 2.44 | 2.40 | 2.22 | 2.24 |
| Strength ratio (%) | MD | 80 | 80 | 81 | 81 | 62 |
| | CD | 17 | 17 | 28 | 28 | 22 |
| Liquid dispersion area (cm²) | | 101 | 96 | 106 | 100 | 145 |
| Liquid evaporation time (min) | | 60 | 60 | 45 | 55 | 20 |

Example 9

A mixed fiber spunbonded web was prepared by the same manner as in Example 1, except that the moving speed of the moving belt was changed. Then, the web was heat bonded by heat embossing under the conditions such that the web had an emboss pattern of an area ratio of 18% and an embossed area of 0.41 mm², and the heating temperature was 105° C. and the linear pressure was 70 N/cm, to obtain a mixed fiber spunbonded web layer 5 having 45 g/m².

The mixed fiber spunbonded web layer 5 obtained was subjected to stretch processing and press processing in the same method as in Example 1, thereby obtaining a mixed fiber spunbonded nonwoven fabric. The mixed fiber spunbonded nonwoven fabric obtained had a basis weight of 45 g/m². The mixed fiber spunbonded nonwoven fabric obtained was evaluated by the method as described above. The evaluation result is shown in Table 3. The touch (11) was evaluated as "I". When this mixed fiber spunbonded nonwoven fabric was stretched in CD, good stretchability was obtained.

Example 10

<Production of Mixed Fiber Spunbonded Web Layer>

The mixed fiber spunbonded web layer 4 obtained in Example 4 was heat bonded by heat embossing under the conditions such that the web layer had an emboss pattern of an area ratio of 18% and an embossed area of 0.41 mm², and the heating temperature was 105° C. and the linear pressure was 70 N/cm, to obtain a mixed fiber spunbonded web having 30 g/m².

The mixed fiber spunbonded web obtained was subjected to stretch processing in the same method as in Example 1, thereby obtaining a mixed fiber spunbonded web layer 5. The mixed fiber spunbonded web layer 5 obtained had a basis weight of 30 g/m².

Subsequently, the mixed fiber spunbonded web layer 1 obtained in Example 1 was heat bonded by heat embossing under the conditions such that the web layer had an emboss pattern of an area ratio of 18% and an embossed area of 0.41 mm², and the heating temperature was 105° C. and the linear pressure was 70 N/cm, to obtain a mixed fiber spunbonded web having 30 g/m².

The mixed fiber spunbonded web obtained was subjected to stretch processing in the same method as in Example 1, thereby obtaining a mixed fiber spunbonded web layer 6. The mixed fiber spunbonded web layer 6 obtained had a basis weight of 30 g/m².

<Production of Mixed Fiber Spunbonded Nonwoven Fabric>

The mixed fiber spunbonded web layer 5 and the mixed fiber spunbonded web layer 6, obtained by the production method as described above, and the mixed fiber spunbonded nonwoven fabric obtained in Example 9 were superposed with each other, in such a manner that the mixed fiber spunbonded nonwoven fabric obtained in Example 9 formed an intermediate layer (a second layer). Then, they were heat bonded by heat embossing under the conditions such that they had an emboss pattern of an area ratio of 18% and an embossed area of 0.41 mm$^2$, and the heating temperature was 120° C. and the linear pressure was 30 N/cm, to obtain a laminated mixed fiber spunbonded nonwoven fabric.

The mixed fiber spunbonded web layer 5 of the mixed fiber spunbonded nonwoven fabric obtained was defined as a surface, and the surface was evaluated in the same manner as described above. The evaluation result is shown in Table 3. The touch (11) was evaluated as "H". When this mixed fiber spunbonded nonwoven fabric was stretched in CD, good stretchability was obtained.

Example 11

The mixed fiber spunbonded web layer 5 and the mixed fiber spunbonded web layer 6, obtained in Example 10, and the mixed fiber spunbonded nonwoven fabric obtained in Example 9 were superposed with each other, in such a manner that the mixed fiber spunbonded nonwoven fabric obtained in Example 9 formed an intermediate layer (a second layer). Then, they were heat bonded by heat embossing under the conditions such that they had an emboss pattern of an area ratio of 18% and an embossed area of 0.41 mm$^2$, and the heating temperature was 120° C. and the linear pressure was 30 N/cm, to obtain a laminated mixed fiber spunbonded nonwoven fabric.

The mixed fiber spunbonded web layer 6 of the mixed fiber spunbonded nonwoven fabric obtained was defined as a surface, and the surface was evaluated in the same manner as described above. The evaluation result is shown in Table 3. The touch (11) was evaluated as "H". When this mixed fiber spunbonded nonwoven fabric was stretched in CD, good stretchability was obtained.

Example 12

The mixed fiber spunbonded nonwoven fabric obtained in Example 11 was stretched in CD by 100%. Then, the mixed fiber spunbonded web layer 5 was defined as a surface, and the surface was evaluated in the same manner as described above. The evaluation result is shown in Table 3. The touch (11) was evaluated as "H". When this mixed fiber spunbonded nonwoven fabric was stretched in CD, good stretchability was obtained.

TABLE 3

| | Example/Comparative Example | Example 9 | | Example 10 | |
|---|---|---|---|---|---|
| First Layer | Fiber form | Mixed fiber | | Mixed fiber | |
| | | b-1 | a-1 | b-1 | a-3 |
| | Weight proportion (%) | 50 | 50 | 30 | 70 |
| | Polymer (part by weight) | B-1 (100) | PP-1 (96) | B-1 (100) | PP-1 (96) |
| | | — | HDPE (4) | — | HDPE (4) |
| | Hydrophilizing agent (part by weight) | — | AE-1 (5) | — | AE-1 (1.8) |
| | Starting temperature for solidification of TPU | 103.7° C. | | 103.7° C. | |
| | Particle number of components insoluble in DMAC solvent in TPU | 150 × 10$^4$ particles/g | | 150 × 10$^4$ particles/g | |
| | TPU shore A hardness | 86 | | 86 | |
| | Molding method | Spunbond | | Spunbond | |
| | Fusion method | Heat embossing | | Heat embossing | |
| | Stretching treatment | CD × 374% | | CD × 374% | |
| | Pressing treatment (area ratio) | 120° C. × 30 N/cm (100%) | | No | |
| | Basis weight (g/m$^2$) | 45 | | 30 | |
| Second Layer | Fiber form | — | — | Mixed fiber | |
| | | — | — | b-1 | a-1 |
| | Weight proportion (%) | — | — | 50 | 50 |
| | Polymer (part by weight) | — | — | B-1 (100) | PP-1 (96) |
| | | — | — | — | HDPE (4) |
| | Hydrophilizing agent (part by weight) | — | — | — | AE-1 (5) |
| | Starting temperature for solidification of TPU | — | | 103.7° C. | |
| | Particle number of components insoluble in DMAC solvent in TPU | — | | 150 × 10$^4$ particles/g | |
| | TPU shore A hardness | — | | 86 | |
| | Molding method | — | | Spunbond | |
| | Fusion method | — | | Heat embossing | |
| | Stretching treatment | — | | CD × 374% | |
| | Pressing treatment (area ratio) | — | | 120° C. × 30 N/cm (100%) | |
| | Basis weight (g/m$^2$) | — | | 45 | |

TABLE 3-continued

| | | | | | |
|---|---|---|---|---|---|
| Third Layer | Fiber form | — | | Mixed fiber | |
| | | | | b-1 | a-1 |
| | Weight proportion (%) | — | — | 50 | 50 |
| | Polymer (part by weight) | — | — | B-1 (100) | PP-1 (96) |
| | | — | — | — | HDPE (4) |
| | Hydrophilizing agent (part by weight) | — | — | — | AE-1 (5) |
| | Starting temperature for solidification of TPU | — | | 103.7° C. | |
| | Particle number of components insoluble in DMAC solvent in TPU | — | | $150 \times 10^4$ particles/g | |
| | TPU shore A hardness | — | | 86 | |
| | Molding method | — | | Spunbond | |
| | Fusion method | — | | Heat embossing | |
| | Stretching treatment | — | | CD × 374% | |
| | Pressing treatment (area ratio) | — | | No | |
| | Basis weight (g/m²) | — | | 30 | |

| | Example/Comparative Example | Example 11 | | Example 12 | |
|---|---|---|---|---|---|
| First Layer | Fiber form | Mixed fiber | | Mixed fiber | |
| | | b-1 | a-3 | b-1 | a-3 |
| | Weight proportion (%) | 30 | 70 | 30 | 70 |
| | Polymer (part by weight) | B-1 (100) | PP-1 (96) | B-1 (100) | PP-1 (96) |
| | | — | HDPE (4) | — | HDPE (4) |
| | Hydrophilizing agent (part by weight) | — | AE-1 (1.8) | — | AE-1 (1.8) |
| | Starting temperature for solidification of TPU | 103.7° C. | | 103.7° C. | |
| | Particle number of components insoluble in DMAC solvent in TPU | $150 \times 10^4$ particles/g | | $150 \times 10^4$ particles/g | |
| | TPU shore A hardness | 86 | | 86 | |
| | Molding method | Spunbond | | Spunbond | |
| | Fusion method | Heat embossing | | Heat embossing | |
| | Stretching treatment | CD × 374% | | CD × 374% | |
| | Pressing treatment (area ratio) | No | | No | |
| | Basis weight (g/m²) | 30 | | 30 | |
| Second Layer | Fiber form | Mixed fiber | | Mixed fiber | |
| | | b-1 | a-1 | b-1 | a-1 |
| | Weight proportion (%) | 50 | 50 | 50 | 50 |
| | Polymer (part by weight) | B-1 (100) | PP-1 (96) | B-1 (100) | PP-1 (96) |
| | | — | HDPE (4) | — | HDPE (4) |
| | Hydrophilizing agent (part by weight) | — | AE-1 (5) | — | AE-1 (5) |
| | Starting temperature for solidification of TPU | 103.7° C. | | 103.7° C. | |
| | Particle number of components insoluble in DMAC solvent in TPU | $150 \times 10^4$ particles/g | | $150 \times 10^4$ particles/g | |
| | TPU shore A hardness | 86 | | 86 | |
| | Molding method | Spunbond | | Spunbond | |
| | Fusion method | Heat embossing | | Heat embossing | |
| | Stretching treatment | CD × 374% | | CD × 374% | |
| | Pressing treatment (area ratio) | 120° C. × 30 N/cm (100%) | | 120° C. × 30 N/cm (100%) | |
| | Basis weight (g/m²) | 45 | | 45 | |

TABLE 3-continued

| | | Mixed fiber | | Mixed fiber | |
|---|---|---|---|---|---|
| Third Layer | Fiber form | b-1 | a-1 | b-1 | a-1 |
| | Weight proportion (%) | 50 | 50 | 50 | 50 |
| | Polymer (part by weight) | B-1 (100) | PP-1 (96) | B-1 (100) | PP-1 (96) |
| | | — | HDPE (4) | — | HDPE (4) |
| | Hydrophilizing agent (part by weight) | — | AE-1 (5) | — | AE-1 (5) |
| | Starting temperature for solidification of TPU | 103.7° C. | | 103.7° C. | |
| | Particle number of components insoluble in DMAC solvent in TPU | $150 \times 10^4$ particles/g | | $150 \times 10^4$ particles/g | |
| | TPU shore A hardness | 86 | | 86 | |
| | Molding method | Spunbond | | Spunbond | |
| | Fusion method | Heat embossing | | Heat embossing | |
| | Stretching treatment | CD × 374% | | CD × 374% | |
| | Pressing treatment (area ratio) | No | | No | |
| | Basis weight (g/m$^2$) | 30 | | 30 | |

| Example/ Comparative Example | | Example 9 | Example 10 | Example 11 | Example 12 |
|---|---|---|---|---|---|
| Lamination method of each layer | | — | Heat embossing | Heat embossing | Heat embossing |
| Processing method after lamination | Stretching treatment | — | No | No | CD × 100% |
| | Pressing treatment (area ratio) | — | No | No | No |
| Surface measured (surface on which liquid was dropped) | | First layer | First layer | Third layer | First layer |
| Basis weight (g/m$^2$) | | 45 | 113 | 113 | 112 |
| Thickness (mm) | | 0.17 | 0.58 | 0.58 | 1.00 |
| Bulk density (g/cm$^3$) | | 0.27 | 0.20 | 0.20 | 0.11 |
| Fiber diameter (μm) | | 20.6 | 21.3 | 21.3 | 21.2 |
| Breathability (cm$^3$/cm$^2$/sec) | | 67 | 40 | 40 | 152 |
| MIU (—) | MD | 1.77 | 2.02 | 2.17 | 2.14 |
| | CD | 2.32 | 2.52 | 2.38 | 2.55 |
| Strength ratio (%) | MD | 56 | 52 | 52 | 48 |
| | CD | 24 | 23 | 23 | 22 |
| Liquid dispersion area (cm$^2$) | | 120 | 52 | 65 | 35 |
| Liquid evaporation time (min) | | 30 | 60 | 45 | 90 |

Example 13

<Production of Mixed Fiber Spunbonded Nonwoven Fabric>

A mixed fiber spunbonded web was prepared by the same manner as in Example 1, except that the moving speed of the moving belt was changed. Then, the web was heat bonded by heat embossing under the conditions such that the web had an emboss pattern of an area ratio of 18% and an embossed area of 0.41 mm$^2$, and the heating temperature was 105° C. and the linear pressure was 70 N/cm, to obtain a mixed fiber spunbonded web 7.

The mixed fiber spunbonded web 7 obtained was subjected to stretch processing in the same method as in Example 1, and was subjected to press processing under the conditions such that the web had a pattern of FIG. 3, an area ratio of 50%, and a width of the pressed portion of 8 mm, and the heating temperature was 105° C. and the linear pressure was 30 N/cm, thereby obtaining a mixed fiber spunbonded nonwoven fabric. The mixed fiber spunbonded nonwoven fabric obtained had a basis weight of 60 g/m$^2$, and a pressed area ratio of 50%. The mixed fiber spunbonded nonwoven fabric obtained was evaluated in the same manner as described above. The evaluation result is shown in Table 4. The touch (11) was evaluated as "I". When this mixed fiber spunbonded nonwoven fabric was stretched in CD, good stretchability was obtained.

Example 14

The mixed fiber spunbonded nonwoven fabric obtained in Example 13 was cut into 250 mm (MD)×250 mm (CD), and the cut nonwoven fabric was rotated 90° in the planar direction. Then, the nonwoven fabric was subjected to press processing in the same method as in Example 13, thereby obtaining a mixed fiber spunbonded nonwoven fabric. The mixed fiber spunbonded nonwoven fabric obtained had a basis weight of 60 g/m$^2$, a pressed area ratio of 75%, and a pressed portion pattern as shown in FIG. 9. The mixed fiber spunbonded nonwoven fabric obtained was evaluated by the method as described above. The evaluation result is shown in Table 4. The touch (11) was evaluated as "I". When this mixed fiber spunbonded nonwoven fabric was stretched in CD, good stretchability was obtained.

Example 15

A mixed fiber spunbonded web was prepared by the same manner as in Example 1, except that the moving speed of the moving belt was changed. Then, the web was heat bonded by heat embossing under the conditions such that the web had an emboss pattern of an area ratio of 18% and an embossed area of 0.41 mm², and the heating temperature was 105° C. and the linear pressure was 70 N/cm, to obtain a mixed fiber spunbonded web 8 having 30 g/m².

The mixed fiber spunbonded web 8 obtained was subjected to stretch processing in the same method as in Example 1, and was subjected to press processing under the conditions such that the web had a pattern of FIG. 4, an area ratio of 24%, and a width of the pressed portion of 2.2 mm, and the heating temperature was 105° C. and the linear pressure was 30 N/cm, thereby obtaining a mixed fiber spunbonded nonwoven fabric. The mixed fiber spunbonded nonwoven fabric obtained had a basis weight of 30 g/m², and a pressed area ratio of 24%. The mixed fiber spunbonded nonwoven fabric obtained was evaluated in the same manner as described above. The evaluation result is shown in Table 4. The touch (11) was evaluated as "I". When this mixed fiber spunbonded nonwoven fabric was stretched in CD, good stretchability was obtained.

Example 16

The mixed fiber spunbonded nonwoven fabric obtained in Example 15 was subjected to press processing under the conditions such that the mixed fiber spunbonded nonwoven fabric had a pattern of FIG. 4, an area ratio of 37%, and a width of the pressed portion of 3.3 mm, and the heating temperature was 105° C. and the linear pressure was 30 N/cm, thereby obtaining a mixed fiber spunbonded nonwoven fabric. The mixed fiber spunbonded nonwoven fabric obtained had a basis weight of 30 g/m², and a pressed area ratio of 37%. The mixed fiber spunbonded nonwoven fabric obtained was evaluated in the same manner as described above. The evaluation result is shown in Table 4. The touch (11) was evaluated as "I". When this mixed fiber spunbonded nonwoven fabric was stretched in CD, good stretchability was obtained.

Example 17

The mixed fiber spunbonded nonwoven fabric obtained in Example 15 was cut into 250 mm (MD)×250 mm (CD), and the cut nonwoven fabric was rotated 90° in the planar direction. Then, the nonwoven fabric was subjected to press processing in the same method as in Example 15, thereby obtaining a mixed fiber spunbonded nonwoven fabric. The mixed fiber spunbonded nonwoven fabric obtained had a basis weight of 31 g/m², a pressed area ratio of 42%, and a pressed portion pattern as shown in FIG. 9. The mixed fiber spunbonded nonwoven fabric obtained was evaluated by the method as described above. The evaluation result is shown in Table 4. The touch (11) was evaluated as "I". When this mixed fiber spunbonded nonwoven fabric was stretched in CD, good stretchability was obtained.

Comparative Example 4

The mixed fiber spunbonded web 8 obtained in Example 15 was subjected to stretch processing described in Example 1 alone, and was evaluated by the same method as described above. The evaluation result is shown in Table 4.

TABLE 4

| Example/Comparative Example | | Example 13 | | Example 14 | | Example 15 | |
|---|---|---|---|---|---|---|---|
| First Layer | Fiber form | Mixed fiber | | Mixed fiber | | Mixed fiber | |
| | | b-1 | a-1 | b-1 | a-1 | b-1 | a-1 |
| | Weight proportion (%) | 50 | 50 | 50 | 50 | 50 | 50 |
| | Polymer (part by weight) | B-1 (100) | PP-1 (96) | B-1 (100) | PP-1 (96) | B-1 (100) | PP-1 (96) |
| | | — | HDPE (4) | — | HDPE (4) | — | HDPE (4) |
| | Hydrophilizing agent (part by weight) | — | AE-1 (5) | — | AE-1 (5) | — | AE-1 (5) |
| | Starting temperature for solidification of TPU | 103.7° C. | | 103.7° C. | | 103.7° C. | |
| | Particle number of components insoluble in DMAC solvent in TPU | 150 × 10⁴ particles/g | | 150 × 10⁴ particles/g | | 150 × 10⁴ particles/g | |
| | TPU shore A hardness | 86 | | 86 | | 86 | |
| | Molding method | Spunbond | | Spunbond | | Spunbond | |
| | Fusion method | Heat embossing | | Heat embossing | | Heat embossing | |
| | Stretching treatment | CD × 374% | | CD × 374% | | CD × 374% | |
| | Pressing treatment (area ratio) | 105° C. × 30 N/cm (50%) | | 105° C. × 30 N/cm (75%) | | 105° C. × 30 N/cm (24%) | |
| | Basis weight (g/m²) | 60 | | 60 | | 30 | |

TABLE 4-continued

| Example/Comparative Example | | Example 16 | | Example 17 | | Comparative Example 4 | |
|---|---|---|---|---|---|---|---|
| First Layer | Fiber form | Mixed fiber | | Mixed fiber | | Mixed fiber | |
| | | b-1 | a-1 | b-1 | a-1 | b-1 | a-1 |
| | Weight proportion (%) | 50 | 50 | 50 | 50 | 50 | 50 |
| | Polymer (part by weight) | B-1 (100) | PP-1 (96) | B-1 (100) | PP-1 (96) | B-1 (100) | PP-1 (96) |
| | | — | HDPE (4) | — | HDPE (4) | — | HDPE (4) |
| | Hydrophilizing agent (part by weight) | — | AE-1 (5) | — | AE-1 (5) | — | AE-1 (5) |
| | Starting temperature for solidification of TPU | 103.7° C. | | 103.7° C. | | 103.7° C. | |
| | Particle number of components insoluble in DMAC solvent in TPU | $150 \times 10^4$ particles/g | | $150 \times 10^4$ particles/g | | $150 \times 10^4$ particles/g | |
| | TPU shore A hardness | 86 | | 86 | | 86 | |
| | Molding method | Spunbond | | Spunbond | | Spunbond | |
| | Fusion method | Heat embossing | | Heat embossing | | Heat embossing | |
| | Stretching treatment | CD × 374% | | CD × 374% | | CD × 374% | |
| | Pressing treatment (area ratio) | 105° C. × 30 N/cm (37%) | | 105° C. × 30 N/cm (42%) | | No | |
| | Basis weight (g/m²) | 30 | | 30 | | 30 | |

| Example/Comparative Example | | Example 13 | Example 14 | Example 15 | Example 16 | Example 17 | Comparative Example 4 |
|---|---|---|---|---|---|---|---|
| Lamination method of each layer | | — | — | — | — | — | — |
| Processing method after lamination | Stretching treatment | — | — | — | — | — | — |
| | Pressing treatment (area ratio) | — | — | — | — | — | — |
| Surface measured (surface on which liquid was dropped) | | First layer | First layer | First layer | First layer | First layer | First layer |
| Basis weight (g/m²) | | 60 | 61 | 30 | 30 | 31 | 30 |
| Thickness (mm) | | 0.22/1.11* | 0.22/1.11* | 0.13/0.52* | 0.13/0.52* | 0.13/0.52* | 0.52 |
| Bulk density (g/cm³) | | 0.16 | 0.25 | 0.10 | 0.12 | 0.13 | 0.06 |
| Fiber diameter (μm) | | 20.2 | 20.2 | 18.6 | 18.5 | 18.7 | 18.2 |
| Breathability (cm³/cm²/sec) | | 219 | 157 | 420 | 320 | 350 | 670 |
| MIU (−) | MD | 2.22 | 2.18 | 2.65 | 2.43 | 2.48 | 2.58 |
| | CD | 2.64 | 2.52 | 2.91 | 2.82 | 2.75 | 2.92 |
| Strength ratio (%) | MD | 23 | 44 | 44 | 40 | 41 | 43 |
| | CD | 24 | 28 | 24 | 20 | 27 | 11 |
| Liquid dispersion area (cm²) | | 94 | 112 | 24 | 27 | 27 | 8 |
| Liquid evaporation time (min) | | 55 | 45 | 135 | 90 | 90 | not less than 180 |

*Thickness: press treated portion/non-press treated portion

POSSIBILITY FOR INDUSTRIAL USE

The mixed fiber spunbonded nonwoven fabric of the present invention has excellent initial hydrophilicity, long-lasting hydrophilicity, liquid dispersibility, liquid transpiration property, softness, resistance to fluff, stretchability and touch, and low stickiness. Therefore, making the best of such properties, the mixed fiber spunbonded nonwoven fabric is suitably used for not only sanitary goods but also medical goods, industrial materials and other materials.

DESCRIPTION OF SYMBOLS

1: Mixed fiber spunbonded nonwoven fabric
2-1: Upper gear roll of Gear processing machine
2-2: Lower gear roll of Gear processing machine
3: Gear pitch
4: Depth of meshing
5: Pressed portion
6: Non-pressed portion

The invention claimed is:

1. A method for producing a mixed fiber spunbonded nonwoven fabric comprising the steps of partially heat fusing a web which comprises 90 to 10% by weight of a long fiber of thermoplastic resin (A) that has been hydrophilization-treated and 10 to 90% by weight of a long fiber of thermoplastic elastomer (B), stretching the web in at least one direction and relaxing the stretched web, and pressing the relaxed web.

2. The method for producing a mixed fiber spunbonded nonwoven fabric according to claim 1, wherein the pressing is carried out on not less than 20% of the area of the relaxed web.

3. The method for producing a mixed fiber spunbonded nonwoven fabric according to claim 1, wherein the pressing is carried out at a melting point of the long fiber of thermoplastic resin (A)−100° C. through a melting point of the long fiber of thermoplastic resin (A)−10° C., and at a linear pressure of 20 N/cm or higher.

4. The method for producing a mixed fiber spunbonded nonwoven fabric according to claim 1, wherein the mixed fiber spunbonded nonwoven fabric has a strength ratio [the ratio of a strength at 20% of an elongation at a maximum strength (elongation at a maximum point) to the maximum strength] in at least one direction of not more than 40% and a bulk density of 0.10 to 0.40 g/cm$^3$.

5. The method for producing a mixed fiber spunbonded nonwoven fabric according to claim 1, wherein the thermoplastic resin (A) is a propylene polymer, and the thermoplastic elastomer (B) is a thermoplastic polyurethane elastomer.

6. The method for producing a mixed fiber spunbonded nonwoven fabric according to claim 1, wherein the thermoplastic resin (A) that has been hydrophilization-treated is obtained by adding 0.1 to 10 parts by weight of a nonionic surface-active agent to 100 parts by weight of the thermoplastic resin (A).

* * * * *